United States Patent
Chai et al.

(10) Patent No.: US 10,479,814 B2
(45) Date of Patent: Nov. 19, 2019

(54) ADENOSINE RECEPTOR ACTIVATION REAGENT AND THE USES OF THEREOF

(71) Applicant: Zhejiang Subtropical Crops Research Institute, Wenzhou (CN)

(72) Inventors: Yiqiu Chai, Wenzhou (CN); Bichun Zhu, Wenzhou (CN); Xiuxiu Peng, Wenzhou (CN); Yiwei Jin, Wenzhou (CN)

(73) Assignee: Zhejiang Subtropical Crops Research Institute, Wenzhou (CN)

( * ) Notice: Subject to any disclaimer, the term of this patent is extended or adjusted under 35 U.S.C. 154(b) by 0 days.

(21) Appl. No.: 15/700,824

(22) Filed: Sep. 11, 2017

(65) Prior Publication Data

US 2017/0369520 A1  Dec. 28, 2017

Related U.S. Application Data

(63) Continuation of application No. 14/805,742, filed on Jul. 22, 2015, now abandoned.

(30) Foreign Application Priority Data

Jul. 27, 2014  (CN) .......................... 2014 1 0360752
May 6, 2015  (CN) .......................... 2015 1 0226745

(51) Int. Cl.
| | |
|---|---|
| *C07H 19/167* | (2006.01) |
| *C07H 19/16* | (2006.01) |
| *A61P 25/16* | (2006.01) |
| *A61P 25/36* | (2006.01) |
| *A61P 25/08* | (2006.01) |

(52) U.S. Cl.
CPC ........... *C07H 19/16* (2013.01); *C07H 19/167* (2013.01); *A61P 25/08* (2018.01); *A61P 25/16* (2018.01); *A61P 25/36* (2018.01)

(58) Field of Classification Search
CPC .................................................. C07H 19/167
See application file for complete search history.

(56) References Cited

U.S. PATENT DOCUMENTS

| | | | |
|---|---|---|---|
| 8,008,060 B2 * | 8/2011 | Cleaver .................... | C12N 1/14 435/254.1 |
| 2013/0045942 A1 * | 2/2013 | Shi ........................ | C07H 19/167 514/46 |
| 2016/0024135 A1 | 1/2016 | Chai et al. | |

OTHER PUBLICATIONS

Entry for Parkinson's disease, Mayo Clinic website, https://www.mayoclinic.org, accessed online on Jan. 17, 2019 (Year: 2019).*
Kostoff et al., Technological Forecasting & Social Change, 2008, 75, p. 226-238. (Year: 2008).*
Yu et al., J. Agric. Food Chem., 2006, 54, p. 3132-3138. (Year: 2006).*
Park et al., Neurosci. Lett., 2004, 363, p. 243-246. (Year: 2004).*
Ahn et al., Int. J. Indust. Entomol., 2008, 17(2), p. 197-200. (Year: 2008).*
Adami et al., *European Journal of Pharmacology* 294 (1995) 383-389, "Effects of repeated administration of selective adenosine $A_1$ and $A_{2A}$ receptor agonists on pentylenetetrazole-induced convulsions in the rat".
Colletti et al., *Heptaology* vol. 23, No. 3, (1996), 506-514. "The Role of Cytokine Networks in the Local Liver Injury Following Hepatic Ischemia/Reperfusion in the Rat".
Daemen et al., *J. Clin. Invest.* 104: 541-549 (1999), "Inhibition of Apoptosis Induced by Ischemia-Reperfusion Prevents Inflammation".
Daemen et al., *Transplantation* vol. 73, 1693-1700, No. 11, (Jun. 15, 2002), "Apoptosis and Inflammation in Renal Reperfusion Injury". Definition of derivative, Oxford English Dictionary, http://www.oed.com/, accessed online on Jan. 11, 2011.
Domanski et al., *Transplantation Proceedings*, 39, 1319-1322 (2007), "Purine and Cytokine Concentrations in the Renal Vein of the Allograft During Reperfusion".
Dunwiddie et al., (1982). *J Pharmacol Exp Ther*, 220(1): 70-76. "Sedative and anticonvulsant effects of adenosine analogs in mouse and rat".
Epstein, M., *Arch Intern Med*, 1992, 152: 1573-84. "Calcium antagonists and renal protection: Current status and future perspectives".
Fan et al., Anal. Chim. Acta, 2006, 567, p. 218-228, "Qualitative and quantitative determination of nucleosides, bases and their analogues in natural and cultured Cordyceps by pressurized liquid extraction and high performance liquid chromatography—electrospray ionization tandem mass spectrometry (HPLC-ESI-MS/MS)".
Franklin et al., *J Pharmacol Exp Ther*, vol. 251, No. 3, pp. 1229-1236 (1989), "Adenosine $A_1$ Receptor Activation Mediates Suppression of (−)- Bicuculline Methiodide-Induced Seizures in Rat Prepiriform Cortex".
Hall, P.A., *Endocrine-Related Cancer* (1999) 6: 3-8, "Assessing apoptosis: a critical survey".
Kaster et al., *Neuroscience Letters* 355 (2004) 21-24, "Adenosine administration produces an antidepressant-like effect in mice: evidence for the involvement of $A_1$ and $A_{2A}$ receptors".
Lee et al., *J Am Soc Nephrol* 15: 102-111, (2004), "$A_1$ Adenosine Receptor Activation Inhibits Inflammation, Necrosis, and Apoptosis after Renal Ischemia-Reperfusion Injury in Mice".

(Continued)

*Primary Examiner* — Jonathan S Lau
(74) *Attorney, Agent, or Firm* — Lathrop Gage LLP

(57) ABSTRACT

The present invention relates to application of N(6)-(2-hydroxyethyl)-adenosine (HEA) and its derivatives as an adenosine $A_1$ receptor agonist in preparation of drug or food, the HEA and its derivatives are used in treatment of diseases relating to adenosine receptor regulator, such as insomnia, pain, convulsion, apoplexia, Parkinson's disease, opioid drug addiction and kidney ischemia reperfusion injury etc. The present invention provides a new method for treatment of the diseases relating to nervous system and kidney.

3 Claims, 15 Drawing Sheets

Specification includes a Sequence Listing.

(56) References Cited

OTHER PUBLICATIONS

Li et al., *Pharmacology, Biochemistry and Behavior* 117 (2014) 151-156, "Sedative and hypnotic activity of $N^6$-(3-methoxyl-4-hydroxybenzyl) adenine riboside (B2), an adenosine analog".
Li et al., *PLOS One* (2013) vol. 8, Issue 6, pp. 1-10. "Anticonvulsant Activity of B2, an Adenosine Analog, on Chemical Convulsant-Induced Seizures".
Malhotra et al., *British Journal of Pharmacology* (1997) 120, 282-288, "Effect of adenosine receptor modulation on pentylenetetrazole-induced seizures in rats".
Mareš, P., *J Neural Transm* (2010) 117:1269-1277 "Anticonvulsant action of 2-chloroadenosine against pentetrazol-induced seizures in immature rats is due to activation of A1 adenosine receptors".
Melnikov et al., *J. Clin. Invest.* 110:1083-1091 (2002), "Neutrophil-independent mechanisms of caspase-1- and IL-18-mediated ischemic acute tubular necrosis in mice".
Millan, M., *Progress in Neurobiology* 70 (2003) 83-244, "The neurobiology and control of anxious states".
Paller et al., J. Clin. Invest. vol. 74, (Oct. 1984), 1156-1164, "Oxygen Free Radicals in Ischemic Acute Renal Failure in the Rat".
Palmer et al., *Transplantation* vol. 52, 640-645, No. 4, (Oct. 1991), "Improved Outcome of Cadaveric Renal Transplantation Due to Calcium Channel Blockers".
Phillis, J. W., *Brain Research*, 509 (1990) 328-330, "The selective adenosine $A_2$ receptor agonist, CGS 21680, is a potent depressant of cerebral cortical neuronal activity".
Smyth et al., *BioTechniques* 32:648-665 (Mar. 2002), "Markers of Apoptosis: Methods for Elucidating the Mechanism of Apoptotic Cell Death from the Nervous System".
Sung et al., *Studies in Mycology* 57: 5-59 (2007), "Phylogenetic classification of Cordyceps and the clavicipitaceous fungi".
Taiwo et al., *Neuroscience* vol. 44, No. 1, pp. 131-135, (1991), "Further Confirmation of the Role of Adenyl Cyclase and of camp-Dependent Protein Kinase in Primary Afferent Hyperalgesia".
Won et al., *J. Pharmacal. Sci.*, 2009, 109, p. 403-412, "Cordycepin Attenuates Neointimal Formation by Inhibiting Reactive Oxygen Species-Mediated Responses in Vascular Smooth Muscle Cells in Rats".
Yang et al., *Nephrol Dial Transplant* (2008) 23: 91-100, "Blockage of JAK/STAT signalling attenuates renal ischaemia-reperfusion injury in rats".
Ye et al., *Regul Peptides* (2010), 161 : 58-66, "L. *carnitine* attenuates oxidant injury in HK-2 cells via ROS-mitochondria pathway".
Zhong et al., *Am J Respir Cell Mol Biol* vol. 32. pp. 2-8, (2005), "Synergy between $A_{2B}$ Adenosine Receptors and Hypoxia in Activating Human Lung Fibroblasts".
Zhou et al., *Neuroscience Research* 48 (2004) 397-404, "A short cerebral ischemic preconditioning up-regulates adenosine receptors in the hippocampal CA1 region of rats".

* cited by examiner

Neurological function score

| Group | Neurological function defect score | | | | | | Median (range) |
|---|---|---|---|---|---|---|---|
| | 0 | 1 | 2 | 3 | 4 | 5 | |
| Sham-operation group | 8 | | | | | | 0 (0,0) |
| Model group | - | 2 | 4 | 2 | | | 2 (1,3) |
| Extract of Cordyceps cicadae | | 2 | 3 | 3 | | | 2 (1,3) |
| HEA 5mg/kg | 1 | 2 | 3 | 2 | | | 2 (0,3) |
| HEA 7.5mg/kg | 2 | 3 | 3 | | | | 1 (0,2) * |
| HEA 12mg/kg | 3 | 3 | 2 | | | | 1 (0,2) * |

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gagaccttca acacccagc                                                  20

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
```

```
atgtcacgca cgatttccc                                                    19
```

```
<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
tcttctgagc ggcgtcg                                                      17

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ttgccaggtc cagttccc                                                     18

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tgggaaacaa cagtggtcag g                                                 21

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
catcagaggc aaggaggaaa ac                                                22

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
aacttagaaa ggggattatg gct                                               23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tcagggaaga atctggaaag gt                                                22
```

ADENOSINE RECEPTOR ACTIVATION REAGENT AND THE USES OF THEREOF

RELATED APPLICATIONS

The present application is a continuation of U.S. application Ser. No. 14/805,742, filed Jul. 22, 2015. U.S. application Ser. No. 14/805,742 claims the priority from China Patent Application No. 201410360752.9 filed on Jul. 27, 2014, and China Patent Application No. 201510226745.4, filed on May 6, 2015. The entireties of these applications including all tables, diagrams and claims are incorporated hereby as reference of the present invention.

TECHNICAL FIELD

The present invention relates to a new adenosine $A_1$ receptor agonist, particularly, relates to N(6)-(2-hydroxyethyl)-adenosine (HEA) and its derivatives as adenosine $A_1$ receptor agonist; and its new application as adenosine $A_1$ receptor agonist in preparation of drug or food for prevention and treatment of the disease relating to adenosine receptor regulator.

Incorporated by reference herein in its entirety is the Sequence Listing entitled "sequence Listing.txt", created Jul. 7, 2015, size of 2 kilobytes.

BACKGROUND OF THE INVENTION

*Cordyceps cicadae* is a *Cordyceps*, in which the body is full of mycelium and multiple fruitbodies grown from head, derived from *Ophiocordyceps sobolifera* (Hill ex Watson) (G. H. Sung, J. M. Sung, Hywel-Jones & Spatafora), *Cicada flammatus* Distant, *Platylomia pieli* koto. In these *Cordyceps, Paecilomyces cicadae* is an important one. Traditional Chinese medicine records that it has efficacies such as sedation and hypnosis, anti-convulsive epilepsy, anti-tugging and slackening, and anti-night cry etc., but no evidence shows which specific substance takes effect, and action mechanism. (Qiu Jie and Song JieMing, Research progress of the pharmacological action of cicada fungus, *Chinese Journal of Ethnomedicine and Ethnopharmacy.*, 2009, 9:4-6; Lei BangXin, Effect of different culture conditions on production of N(6)-(2-hydroxyethyl)adenosine by *Cordyceps pruinosa, Mycosystema.*, 15 Jan. 2014, 33 (1): 103-113).

The results of many studies suggest that adenosine receptor is closely related to physiological effects such as neuronal excitation, sports ability regulation etc. It has effect on the action mechanism of effective drugs for treatment of schizophrenia, depression, epilepsy and anxiety (Franklin P H, Zhang G, Trpp E D, Murray T F, 1989. Adenosine $A_1$ receptor activation mediates suppression of (−)-bicuculline methiodide-induced seizures in rat prepiriform cortex. *The Journal of Pharmacology and Experimental Therapeutics.* 251(3):1229-1236; Lai D M, Tu Y K, Liu I M, Cheng J T 2005, Increase of adenosine $A_1$ receptor gene expression in cerebral ischemia of Wistar rats Neuroscience Letters 387: 59-6; Dunwiddie T V, Worth T, 1982. Sedative and anticonvulsant effects of adenosine analogs in mouse and rat. *The Journal of Pharmacology and Experimental Therapeutics.*, 220(1): 70-76; Ismayilova N, Crossman A, Verkhratsky A et al. Effects of adenosine $A_1$, dopamine D1 and metabotropic glutamate 5 receptors-modulating agents on locomotion of the reserpinised rats [J]. *Eur J Pharmacol*, 2004, 497(2): 187-195).

Adenosine receptor, as an excitatory neurotransmitter, is distributed at each part of the body, it is comprised of four subtypes of $A_1$, $A_{2a}$, $A_{2B}$, $A_3$, and these four subtypes are all G-protein-coupled receptors. Wherein, $A_1$ receptor is most sensitive to adenosine, and has most extensive actions. $A_{2A}$ receptor is an important immune molecule of human body, and it is closely related to inflammatory reaction. $A_1$ and $A_{2a}$ receptor widely participate in regulation of many physiological and pathological processes such as sleep, emotion etc. by adenosine. Because of lack of specific ligand to $A_{2B}$ receptor, at present the studies on $A_{2B}$ receptor are not deep, but Zhou and Zhong et el. have mentioned that under certain pathological conditions, high aggregation of adenosine can activate $A_{2B}$ receptor, and have found that $A_{2BR}$ can increase release of IL-6 by astrocyte, indicating $A_{2B}$ receptor possibly participates in inflammatory process. The level of $A_3$ receptor in brain and the level of its affinity to adenosine are much lower than $A_1$ and $A_{2A}$ receptors, and its physiological action is unknown until now (Wang RenYe and Pan JianChun, Biological effects of adenosine and its receptor in nervous system, *Foreign Medical Sciences-Section of Pharmacy*, 2006 August Vol 33(4); Zhou A M, Li W B, Li Q J, et al. A short cerebral ischemic preconditioning up-regulates adenosine receptors in the hippocampal $CA_1$ region of rats [J]. *Neurosci Res*, 2004, 48(4): 397-404. Zhong H, Belardinelli L, Maa T, et al. Synergy between $A_{2B}$ adenosine receptors and hypoxia in activating human lung fibroblasts [J]. *Am J Respir Cell Mol Biol*, 2005, 32(1): 2-8).

Many studies show that the selective $A_1$ adenosine receptor agonist, as endogenous neuroprotective substance, has multiple neuroprotective functions: for example, a study by Taiwo et al proved that after $A_1$ receptors on sensory nerve ending is activated, they can inhibit adenylyl cyclase (AC), and reduce the intracellular concentration of second messenger cyclic adenosine monophosphate (cAMP), producing analgesic effect; Kaster et al found that the antidepressant effect of adenosine seems to be achieved by activating $A_1$ receptor and $A_{2A}$ receptor; the experiment by Millan M J shows anxiety-causing and anti-anxiety effect are respectively related to blocking and agonizing $A_1$ receptor, mice with A1R gene deletion have more anxiety (Taiwo Y O, Levine J D. Further confirmation of the role of adenyl cyclase and of cAMP-dependent protein kinase in primary afferent hyperalgesia [J]. Neuroscience, 1991, 44(1): 131-135; Kaster M P, Rosa A O, Rosso M M, et al. Adenosine administration produces an antidepressant like effect in mice: evidence for the involvement of $A_1$ and $A_{2A}$ receptors [J]. *Neurosci Lett*, 2004, 355(1): 21-24; Millan M J. The neurobiology and control of anxious states [J]. *Prog Neurobiol*, 2003, 70(2): 83-244).

Adenosine $A_1$ receptor is a glycoprotein containing 326 amino acids, its molecular weight is 36,600. Activating $A_1$ receptor can take effect in neuron protection. At present its possible mechanism is considered as follow: on one hand, $A_1$ receptor can inhibit release of excitatory neurotransmitter such as glutamic acid, and protect cells by decreasing excitability of cells; one the other hand, activating $A_1$ receptors on postsynaptic membrane can increase intracellular potassium efflux, thereby protecting neuron by reduced excitability. (Zong KaiQi, Research progress of effect of adenosine $A_1$ receptor, *Chinese Pharmacological Bulletin.*, 2008, 24(5): 573~6).

In the early years, Jacobson K A et al. reported that adenosine was hindered to be used as clinical drug due to its metabolic unstability. Thereafter, some stable analogues were successively synthesized, these compounds are mainly aimed at adenosine N(6)-, 2- and 5'-position modifications.

According to document record, N(6)-replaced adenosine analogues are proved to have $A_1$ receptor selectivity, for example CPA and CHA have 400~800 fold of $A_1$ selectivity, CCPA has 1500 fold of $A_1$ selectivity, S-ENBA has a stronger $A_1$ selectivity of up to 4700 fold. The 5'-replaced adenosine analogue NECA has been widely used in explaining the biological effect caused by $A_2$ receptor activation. In the structural modification of other riboses, replacement at 2'-position can completely lose the affinity, the un-replaced hydroxy at 3'-position is essential to high potency. (Kenneth A. Jacobson, Pharmacology and structure-activity relationship of adenosine receptor, *Progress in Pharmaceutical Sciences*, 1992, Vol 16 (4)).

Most of the existing $A_1$ agonists are N(6)-replaced adenosine derivatives, including CCPA, CHA, and CPA etc, all of them have strong selectivity to the $A_1$ receptor.

SUMMARY OF THE INVENTION

The inventors of the invention surprisingly found that N(6)-(2-hydroxyethyl)-adenosine (HEA) and its derivatives are a new adenosine receptor agonist. They all have strong selectivity to adenosine $A_1$ receptor. They regulate neuroprotective and renal protective functions by specifically bonding $A_1$ receptor and producing a series of physiological and biochemical activities.

On one hand, the present invention relates to a new agonist of adenosine receptor, the agonist includes HEA or its derivatives.

In some specific embodiments, said adenosine receptor is one or more of adenosine $A_1$, $A_{2A}$, $A_{2B}$, $A_3$ receptors.

In some preferred embodiments, the adenosine receptor is the $A_1$ receptor.

In some specific embodiments, the HEA or its derivatives are a new agonist specifically bonding to the $A_1$ receptor.

In some embodiments, said N(6)-(2-hydroxyethyl)-adenosine (HEA) has the following structure

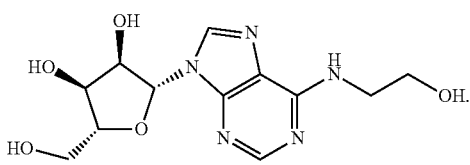 [SMILES: OCCNc1ncnc2c1ncn2[C@@H]1O[C@H](CO)[C@@H](O)[C@H]1O]

In some other specific embodiments, the derivatives of said HEA have the following general formula (1)

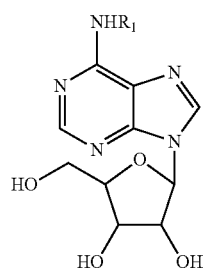

(1)

wherein R1 is a branched or linear alkyl or hydroxyl group. In some preferred embodiments, R1 is $C(CH_3)_2CH_2OH$, $CH(CH_3)CH_2OH$ or $C(CH_3)_3$.

In additional specific embodiments, an artificially synthesized HEA and the HEA extracted from natural product both have functions of neuroprotection and kidney protection etc.

On the other hand, the present invention provides an application of the HEA and its derivatives in preparation of nervous system or kidney protector for prevention or treatment of convulsion, pain, apoplexia, Parkinson's disease or opioid drug addiction, sleep disorder etc.

Another objective of the invention is to provide a drug for prevention and treatment of nervous system such as convulsion, pain, stroke, Parkinson's disease, drug addiction, sleep disorder or renal diseases etc, wherein the drug includes HEA and its derivatives.

Yet another objective of the invention is to provide a food for prevention or treatment of nervous system such as convulsion, stroke, Parkinson's disease, drug addiction, sleep disorder or renal diseases etc, wherein the food includes the HEA and its derivatives.

In a further aspect, the present invention aims to prove that the HEA is the adenosine $A_1$ receptor agonist by an adenosine receptor affinity experiment and a combination addition adenosine receptor antagonist experiment, and its effect of prevention and treatment of nervous system such as convulsion, pain, stroke, Parkinson's disease, drug addiction, sleep disorder or renal diseases etc is obtained via the adenosine $A_1$ receptor.

Preferably, according to said application or agent, said agent is used as drug or food.

Preferably, in the above-described agent or application, said agent is food, including health care food.

Preferably, according to said application or reagent, said reagent can be used in application of treatment of ischemia reperfusion impairment injury in kidney transportation, and inhibition of inflammation and apoptosis in renal failure etc.

In some other preferred embodiments, the HEA is derived from *Cordyceps* or microorganism or extract of microorganism, or extract of microorganism culture. Preferably, the HEA is obtained by isolation from *Cordyceps cicadae, Ophiocordyceps sinensis* (Berk.) G. H. Sung, J. M. Sung, Hywel-Jones & Spatafora, *Cordyceps militaris* (L.) Link, and its artificial culture, and it can also be obtained by synthesis. Preferably, the HEA is obtained by extracting the culture of *Paecilomyces cicadae*, its fruiting body or coremium, culture of mycelium.

The analgesic effect of the HEA can be found in invention patent of China, for example, China Patent Application 200410094511.0, the entirety of this patent application is incorporated hereby as reference of the present invention; the renal protective effect of the HEA can be found in invention patent of China, for example China Patent Application 201280049909.5, the entirety of this patent application is incorporated hereby as reference of the present invention. In the present invention, a drug combination method is firstly introduced, and the action mechanism of the HEA is further speculated by adding a selective $A_1$ receptor antagonist, and the HEA is preliminarily determined as the $A_1$ receptor agonist.

*Cordyceps cicadae* has similar function with *Cordyceps sinensis*, and can be an alternative of the later one, it has multiple regulation activities, but the chemical nature and action mechanism of neuroprotection such as sedation, hypnosis, anti-convulsion etc and kidney protection of the *Cordyceps cicadae* have not been reported. In addition, the applications of prevention or treatment of diseases such as stroke, Parkinson's disease and drug addiction etc. of

*Cordyceps cicadae, Cordyceps militaris* are also first mentioned, and they has new value because they contains the HEA.

Therefore, another aspect of the present invention provides an agent for prevention or treatment of stroke, Parkinson's disease and drug addiction, the agent includes culture of *Paecilomyces cicadae*, its fruiting body or coremium, extract of mycelium culture.

Preferably, the extract includes the HEA.

This study, based on animal experiments, found that the HEA and its derivatives have function of prevention and treatment of diseases relating to the adenosine $A_1$ receptor. Further studies found that protective effect of the HEA can be attenuated by $A_1$ receptor antagonist, suggesting the HEA and its derivatives, as a novel $A_1$ adenosine receptor agonist, can be used in treatment of multiple diseases such as sedation, insomnia, pain, convulsion, apoplexia, Parkinson's disease, addiction or acute renal failure caused by kidney ischemia reperfusion etc.

The present invention also provides a method for treatment or prevention of convulsion, pain, insomnia, apoplexia, Parkinson's disease or opioid drug addiction in mammal or human, wherein the HEA and its derivatives are given to mammal or human.

Preferably, the given HEA and its derivatives are in form of tablet, aqueous solution, mixture, dry mixture etc.

Preferably, these drugs include other adjuvant, for example stabilizer etc.

Preferably, said HEA is derived from *Cordyceps, Cordyceps militaris, Paecilomyces cicadae* fungus or culture extract of this fungus.

Therefore, the present invention has extracted the effective active ingredient HEA from *Cordyceps cicadae* and conducted a series of animal experiments, and investigated the effect of the HEA in treatment of nervous system and kidney diseases relating to the adenosine $A_1$ receptor, and found that it can act as agonist of denosine $A_1$ receptor, and play a role in medical application; and investigated the affinity between HEA and adenosine $A_1$ and A2 receptors, by an adenosine receptor affinity experiment and a combination addition of adenosine receptor antagonist experiment, the result suggests that HEA has high affinity with the adenosine $A_1$ receptor, and proves that HEA is a new selective adenosine $A_1$ receptor agonist. Because the types of clinically available safe selective adenosine $A_1$ receptor agonist are limited, the *Cordyceps* such as *Cordyceps cicadae, Cordyceps sinensis, Cordyceps militaris* etc. have very high medicinal and food value because it contains such a active ingredient. The present invention is expected to be developed as a potential drug for prevention of nervous system disease and kidney protection, and can be made into relevant functional food, health care product for the application beneficial to diseases.

The Origin of HEA can be Extraction from Natural Product or Artificial Synthesis Extraction from Natural Product The present invention extracted and isolated a natural active compound HEA from *Cordyceps cicadae* by chemical method, and by pharmacology tests found that the HEA, as an adenosine $A_1$ receptor agonist, can be used in preparation of drug for prevention of nervous system disease such as convulsion etc.

The present invention used artificially cultured *Cordyceps cicadae* as raw material, and the preparation process is as follow: fruitbody of the *Cordyceps cicadae* was refluxed in 50% ethanol, the extract was isolated by a membrane, and purified with macroporous resin and Sephadex LH20 column, obtaining the single active ingredient of HEA.

The structural formula of the HEA is as follow:

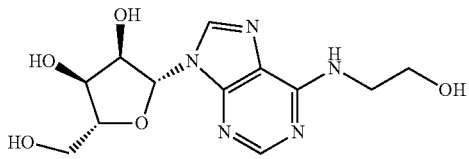 [SMILES: OCCNc1ncnc2c1ncn2[C@@H]1O[C@H](CO)[C@@H](O)[C@H]1O]

Its molecular formula is $C_{12}H_{17}N_5O_5$, its molecular weight is 311.297 and its chemical name is N(6)-(2-hydroxyethyl)-adenosine.

The extracting and purifying method of the HEA can refer to the above patents.

Said HEA of the present invention can be obtained by extracting and isolating from *Cordyceps* fungus which produces HEA such as *O. sinensis, Cordyceps militaris, Cordyceps pruinosa, Ophiocordyceps sinensis* etc. The HEA can be a product isolated from the culture of above-described *Cordyceps* fungus such as *Paecilomyces cicadae* etc, and such a product can be obtained by isolating from fruitbody, mycelium, spore, myceliumculture medium. The HEA can also be derived by artificial chemical synthesis, and also be directly purchased commercially.

Artificial Synthesis

The HEA or its derivatives of the present invention can also be artificially synthesized.

Definitions

"Convulsion" is a cerebral nerve functional disorder induced by multiple reasons, its clinical manifestation is sudden ankylosing and myoclonic twitch of general or local muscle groups, and it is often accompanied by conscious disturbance. If the patient do not seek medical attention in time and take spasmolysis action, his/her life may be threatened. Also, convulsion tends to occur repeatedly, its twitch behaviour can be relieved in a short time, but the pathological change progressively develops over a long time. At present, multiple drug combination treatment of convulsion is very common, but most of them may cause toxicity and side effect and adverse reaction.

"Cerebral ischemia (cerebral infarction or stroke)" is a very common central nerve lesion, it has serious disability rate and high mortality. According to an investigation by Chinese Medical Association: at present, stroke has become the first cause of crippling and death in city and country population in China. In diagnosis and therapy of cerebral ischemic stroke, underestimate and misdiagnose are serious; its admission rate is only about 6%, being much lower than about 30% in the developed countries, furthermore, there are no truly reliable and effective drugs being beneficial to cerebral infarction patients.

"Parkinson's disease (PD)", also called chorea festinans, is one of the most common neurodegenerative diseases. Epidemiology shows that its morbidity is 15-328/100 thousand population, about 1% in population of >65 years; its morbidity is 10-21/100 thousand population/year. The greatest danger of this disease is the life quality of the patients are severely reduced, and unable to look after himself, and multiple complications such as sleep disorder etc. often occur.

"Sleep disorder" refers to various dysfunctions in sleep-awakening procedure. According to incomplete statistics, various types of sleep disorder patients account for 38% of the population in China, being higher than 27% of the world. Besides effecting the mental state, chronic sleep deficit can also reduce human immunity, thus causing a variety of diseases. Study shows that sleep disorder is associated with multiple diseases such as diabetes, stroke, epilepsy, dementia, children's mental retardation, kidney function impairment, sexual dysfunction etc.

"The opioids drugs" includes natural opium alkaloid such as morphine or artificially synthesized analgesic such as pethidine, their addiction is caused by the fact: after morphine is repeatedly used by some chronic pain patients, its potency may be gradually attenuated, forming a resistance, that is, the amount of the morphine is gradually increased and time interval of administration is shortened. The patients may have addiction and produce dependence, including psychic dependence and physical dependence. Once the drug is stopped, a withdrawal symptom will occur after 6-10 hours, and dysphoria, insomnia, pain, runny nose, streaming eyes, sweating, tremor, vomiting, diarrhoea, prostration may occur, even their life are threatened. Such patients all have strong desire for the drug, and may do anything to obtain the drug, this not only severely damage health of the drug user, but also cause severe social problems.

"Renal ischemia reperfusion injury" is a main cause of acute kidney failure, it also possibly related to development of some chronic kidney disease, and acute renal failure is that the ability of kidney scavenging toxic substance in blood being rapidly decreased, resulting in accumulation of metabolic wastes such as urea etc. in blood. Result of one investigation shows that morbidity of kidney disease patient above 40 years is about 8-9% in China, final phase patient of the renal failure ultimately can only select kidney transportation or life-long blood purification, this will place a large economic and mental burden on his/her family.

Here, "food" refers to any substance can be eaten by human or mammal. Such food also includes any health care food, functional food, or generally understood food, it can be in form of beverage, tablet, solution etc. These foods may be in form of solid, semi-solid, fluid.

"Drug agent" is an agent with ordinary meaning in the art, it can be tablet, solvent, semi-solid or injectable liquid etc. Here, "drug" can be in a form of drug for treatment of disease and it can also be in form of heath care drug.

Beneficial Effect

The present invention provides a new agonist of adenosine receptor, specifically, it provide a new agonist of $A_1$ adenosine receptor. This new agent provides the treatment or prevention of such diseases with a new approach.

DETAILED DESCRIPTION OF THE EMBODIMENTS

Figure 1A:
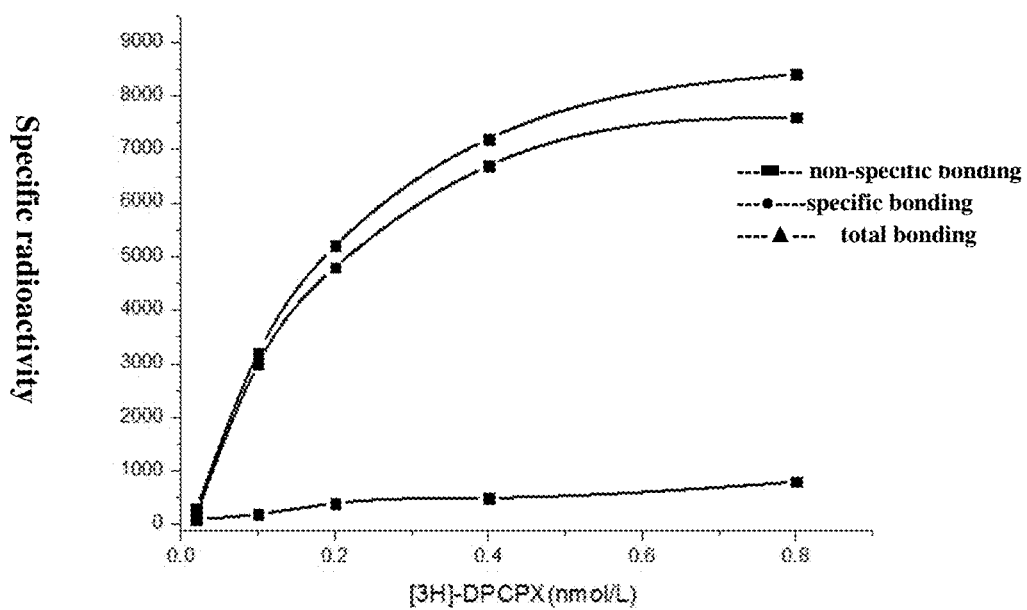
FIGS. 1A-B shows a saturation curve of binding of [$^3$H]-DPCPX with rat cerebral cortex receptor (FIG. 1A) and Scatchard plot (FIG. 1B). Note: B. radionuclide binding protein; F. floating protein (Kd=0.12 nmol/L, Bmax=2140 fmol/mg protein).

Example 1. HEA is a Selective Agonist of $A_1$ Receptor

Preparation of Receptor Protein

Using Wistar rat, head was cut and the brain was removed, and cerebral cortex and striatum were separated, respectively weighed, added into 10 fold volume of ice-cooled Tris-HCL buffer solution (50 mM, PH7.5) according to 1:10, the tissue is homogenized, after the suspension was centrifuged the supernatant was discarded, the above-described solution wash was repeated for 3 times, centrifuged again and the supernatant was discarded, the precipitate was again mixed in 50 mM Tris-HCL buffer solution, the protein concentration in rat cerebral cortex determined by Coomassie Brilliant Blue Method (Bradford method) was 0.8 mg/ml, the protein content in rat striatum brain tissue homogenate was 1.3 mg/ml. After subpackage stored at −80□ for subsequent use (Li M, Kang R X, Shi J G, Liu G T, Zhang J J, 2013. Anticonvulsant Activity of B2, an Adenosine Analog, on Chemical Convulsant-Induced Seizures, *PLoS One* June 25; 8 (6):e67060)

Aadenosine Receptor Ligand Binding Test

To a reaction tube, protein and corresponding ligand (adenosine $A_1$ receptor ligand binding experiment: rat cerebral cortex brain tissue homogenate and corresponding ligand is 0.2 nM binding of [3H] DPCPX; adenosine A2A receptor ligand binding experiment: rat striatum brain tissue homogenate and corresponding ligand are 0.75 nM binding of [3H]MSX-2) were added, and saturation curves of binding of [$^3$H]-DPCPX ([$^3$H]-MSX-2) with rat cerebral cortex adenosine $A_1$ (rat striatum adenosine $A_{2A}$R) were respectively determined, and equilibrium dissociation constant were calculated by Scatchard Linear Transformation Method (Kd value of $A_1$ binding was 0.14 nmol/L, Bmax was 2290 fmol/mg; Kd value of $A_{2A}$ binding was 11.48 nmol/L, Bmax was 5657 fmol/mg).

To a detect tube the HEA with different concentration ($10^{-9}$, $10^{-8}$, $10^{-7}$, $10^{-6}$, $10^{-5}$ mol/L) were added, mixed well, then incubated at 25° C. in water bath on shaking table for 30 min, the reaction liquid was drawn by a cell collector, passed the GF/B glass filter membrane (Watman), reaction was terminated, washed 3 times with Tris-HCl buffer solution, each time 3 ml, the filter membrane was removed and dried, then put into a scintillation vial containing 4 ml of scintillation solution to determine radioactivity. A radioactivity count to the filter membrane was conducted by a scintillation counter. Corresponding 3[$^3$H]-DPCPX or [$^3$H]-MSX-2 binding percentage were determines when compounds of different concentration were present. (Li W, Wang Y F, Li M, YUE Z G, Shi J G, Zhang J J, 2011, Sedative and hypnotic effects of a novel ligand YZG-404 for adenosine $A_1$ receptor, *J Int Pharm Res*, Vol. 38, No. 3, June).

Test Result

Figure 1B:
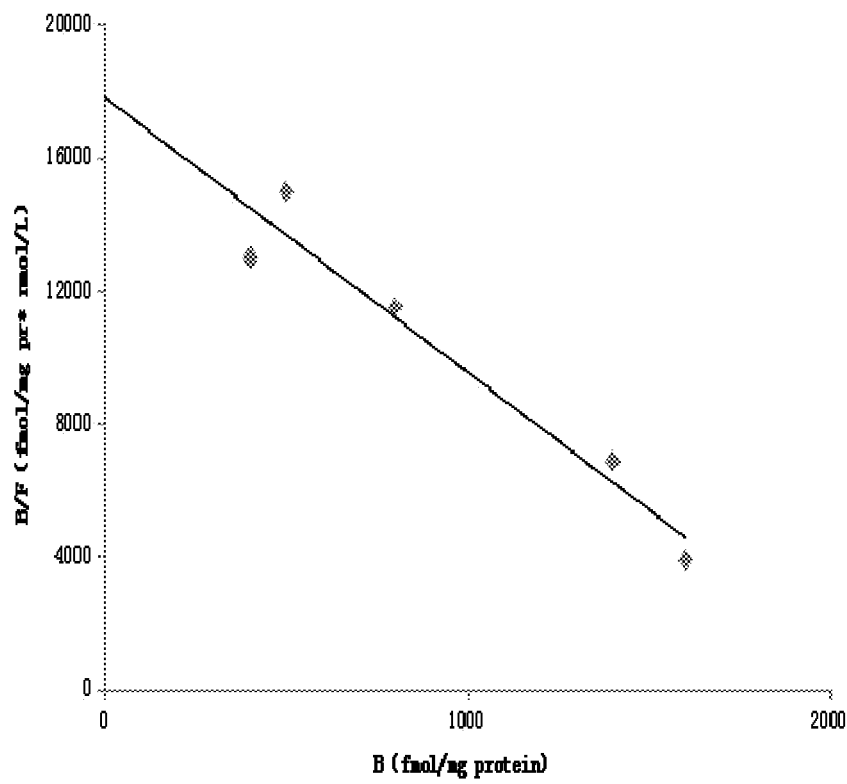
Figure 1C:
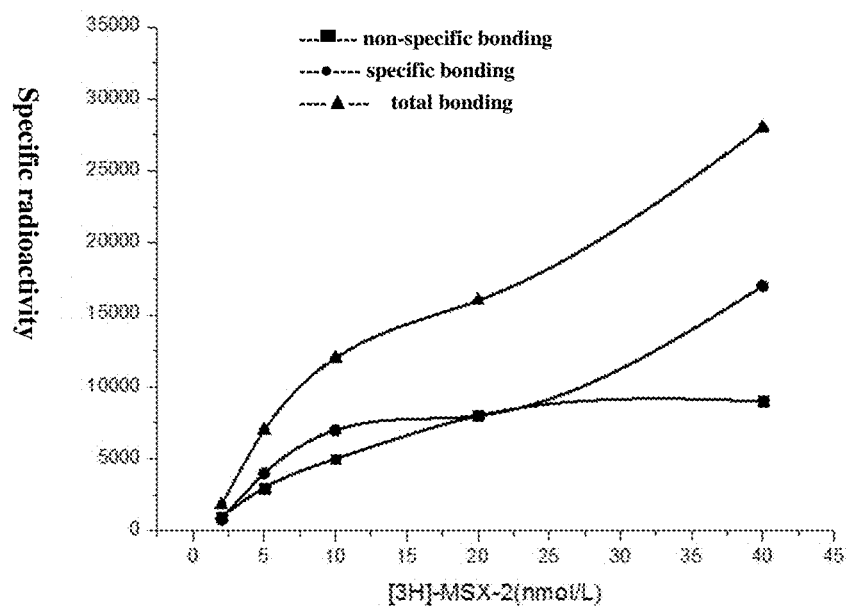
FIGS. 1C-D shows a saturation curve of binding of [$^3$H]-MSX-2 with rat cerebral cortex receptor (FIG. 1C) and Scatchard plot (FIG. 1D). Note: B. radionuclide binding protein; F. floating protein (Kd=10.90 nmol/L, Bmax=5235 fmol/mg protein).
Figure 1D:
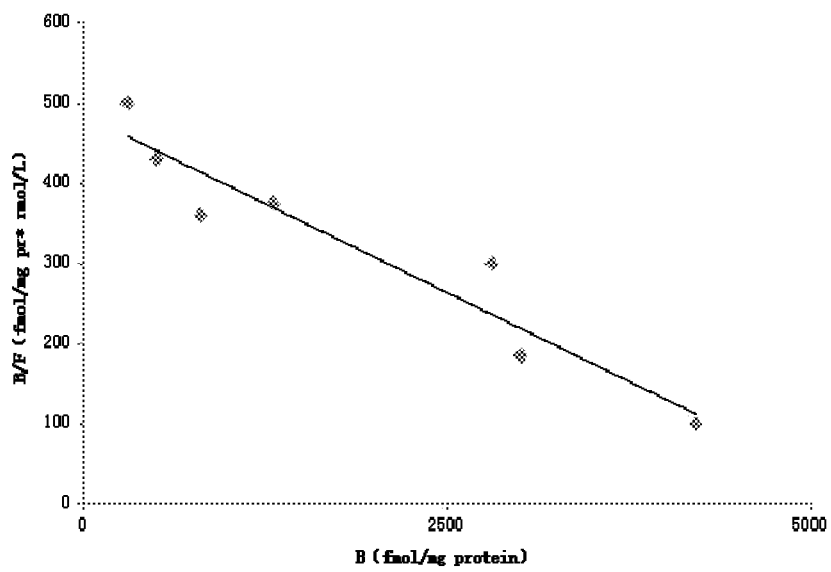

The Ki value of competitive binding of the HEA with the adenosine $A_1$ receptor determined by experiment was 89.5 nmol/L, Ki value of competitive binding with the adenosine $A_{2A}$ receptor was about 8921.4 nmol/L. the affinity of the HEA to adenosine $A_1$ receptor is 100 fold of that to adenosine $A_{2A}$ receptor, the result suggests that HEA has high selectivity to $A_1$ receptor (FIGS. 1A-1B).

Affinity Experiment of Artificially Synthesized HEA and its Derivatives

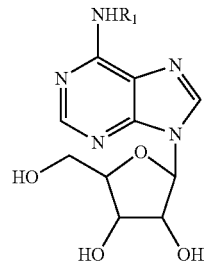

(1)

Wherein, four substances of HEA (artificially synthesized), R1 being $C(CH_3)_2CH_2OH$ (derivative 1), $CH(CH_3)CH_2OH$ (derivative 2) or $C(CH_3)_3$ (derivative 3) were conducted similar test as this experiment, the determined result of the artificially synthesized HEA and its derivative 1-3 were similar to the HEA (specific experiment date is omitted), the result also suggests that the artificially synthesized HEA and its derivative 1-3 have high selectivity to $A_1$ receptor.

Example 2. Application of HEA in Anti-Convulsion 2.1 Animal Model and Administration Method Male ICR mouse, 18~22 g; purchased from Animal Experiment Center of Wenzhou Medical University. Before experiment, animals were adapted to environment for at least 5 days. Kept at 25□, food and water were freely fed. Based on the weight, the healthy male ICR mice were randomly divided into control group (1% DMSO, ip), model group, CCPA group (0.1 mg·kg$^{-1}$, ip), HEA group (15 mg/kg, 40 mg/kg, 60 mg/kg), DPCPX group (2 mg·kg$^{-1}$, ip), ZM241385 group (1 mg·kg$^{-1}$, 5 mg·kg$^{-1}$, ip), DPCPX+HEA (2 mg·kg$^{-1}$+40 mg/kg, ip) group and ZM241385+HEA (1 mg·kg$^{-1}$+40 mg/kg, 5 mg·kg$^{-1}$+40 mg/kg ip) group. Wherein, 10 min before administration, the adenosine $A_1R$ receptor antagonist DPCPX (or $A_2R$ receptor antagonist ZM241385) were peritoneal injected, after 15 min of administration pentylenetetrazole (100 mg·kg$^{-1}$, ip) was given to induce mouse convulsion; in alone antagonist group, after 5 min of the antagonist pentylenetetrazole (100 mg·kg$^{-1}$, ip) was given, the reaction of mouse to PTZ induced convulsion was observed.

2.2 Detection Index

The survival time and mortality after convulsion were respectively recorded for each group.

2.3 Results of the Tests

Figure 2A:
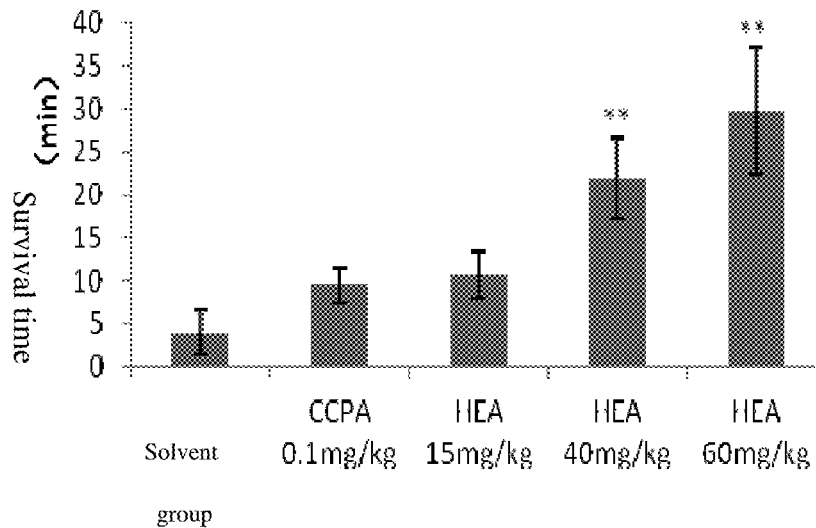
FIG. 2A shows effect of the HEA (15 mg/kg, 40 mg/kg, 60 mg/kg, ip) on incidence of pentylenetetrazole induced convulsion, the result shows that HEA (40 mg/kg, ip) can significantly extend the survival time, exhibiting an anti-convulsion effect (n=8; *P<0.05,**P<0.01 compared with control group).
Figure 2B:
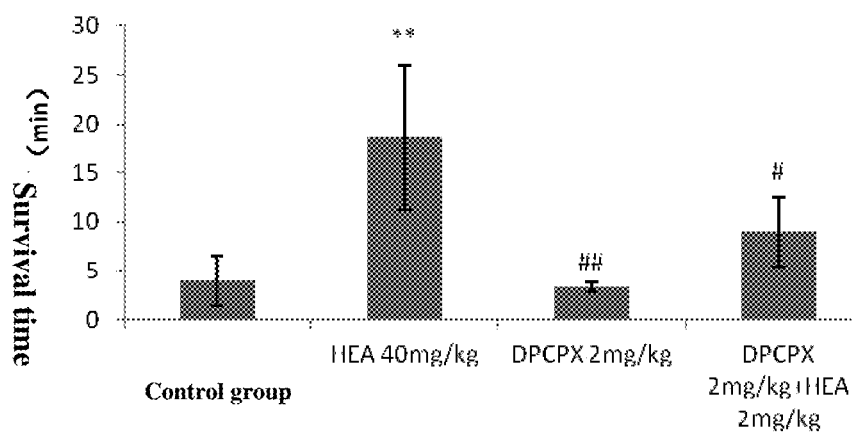
FIG. 2B shows effect of an adenosine $A_1$ receptor selective antagonist on the anti-convulsion action of the HEA, the DPCPX can significantly reduce the anti-convulsion effect of the HEA (n=8; *P<0.05, **P<0.01 compared with control group, #P<0.05, ##P<0.01 compared with drug group HEA 40 mg/kg).
Figures 2C, 3A:
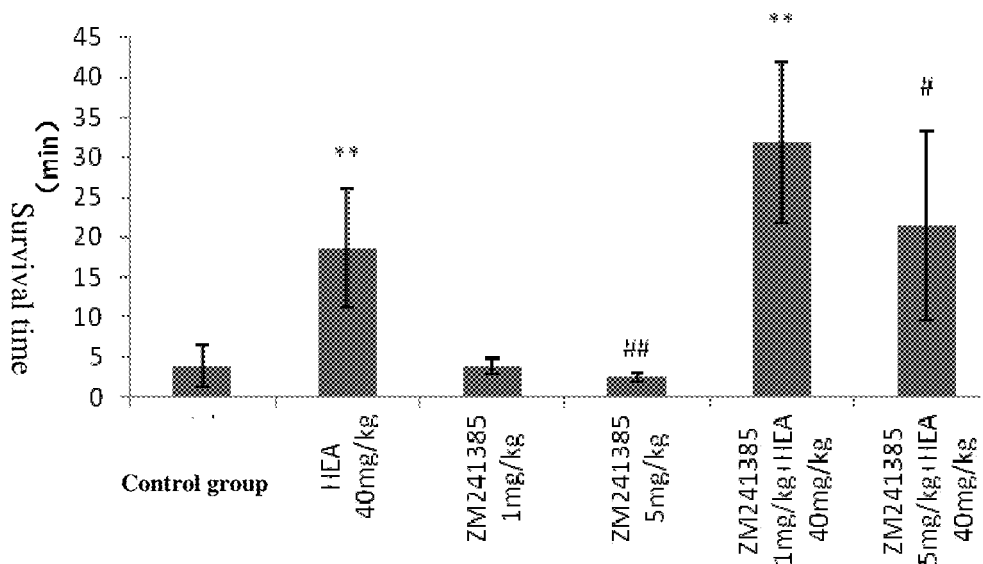
FIG. 2C shows effect of an adenosine $A_{2A}$ receptor selective antagonist on the anti-convulsion action of the HEA, and Zm241385 has no significant effect on the anti-convulsion action of the HEA (n=8; *P<0.05, **P<0.01 compared with control group, #P<0.05, ##P<0.01 compared with drug group HEA 40 mg/kg).
FIG. 3A shows dMCAO cortex rat neurologic function score of an extract of *Cordyceps cicadae* (1500 mg/kg) and the HEA (5 mg/kg, 7.5 mg/kg, 12 mg/kg, ip); the result shows that compared with model group, the HEA can significantly improve neurological function of the injured brain (n=8; *P<0.05, **P<0.01 compared with model group).
Figure 3B:
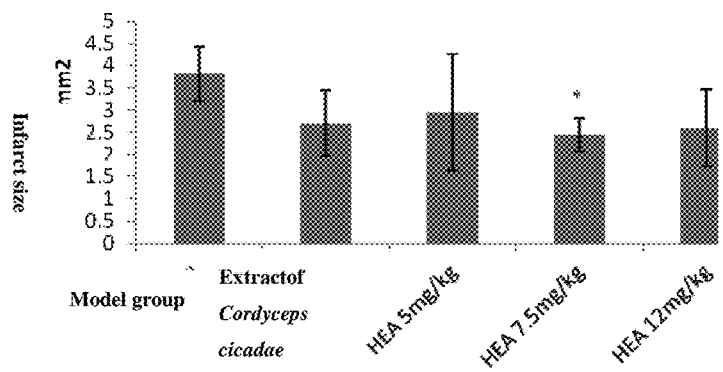
FIG. 3B shows TTC-staining measured infarct size of dMCAO cortex by extract of *Cordyceps cicadae* (1500 mg/kg), the HEA (5 mg/kg, 7.5 mg/kg, 12 mg/kg, ip); the result shows that, compared with the model group, the HEA (7.5 mg/kg, ip) can significantly reduce the infarct size of the injured brain (n=8; *P<0.05, **P<0.01 compared with the model group).
Figure 3C:
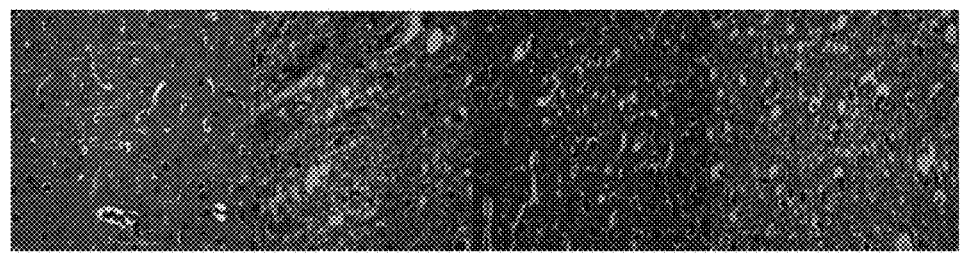
FIG. 3C shows protective effect of the HEA (7.5 mg/kg, ip) group to cerebral ischemia of dMCAO cortex and combination DPCPX (1 mg/kg, ip) blocking the brain protective effect of the HAE and rat brain histomorphology staining HE (400×), the result shows that, compared with the model group, the HEA group can improve cell swelling degree and nuclear aberration, and increases cell number.
Figure 3D:
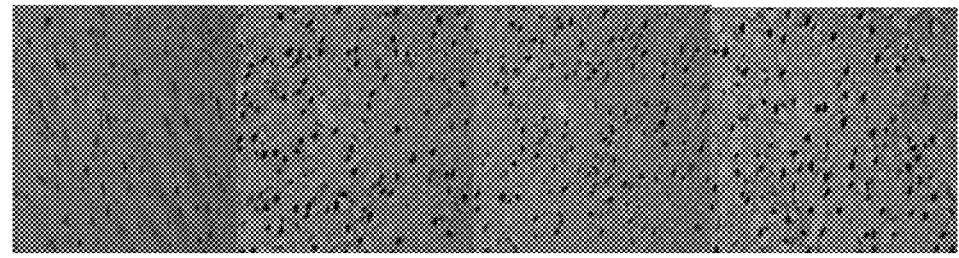
FIG. 3D shows protective effect of HEA (7.5 mg/kg, ip) group on cerebral ischemia of dMCAO cortex and combination DPCPX (1 mg/kg, ip) blocking brain protective effect of the HAE and tunnel detection of rat brain cortex apoptosis (400×), results show that, compared with model group, the HEA group can significantly reduce the apoptosis rate of rat cerebral cortex infarction ischemic penumbra.

The results of animal behavior test suggest that HEA 40 mg·kg$^{-1}$ group can very significantly reduce the mortality of mouse convulsion induced by pentylenetetrazole. In addition, specific $A_1$ receptor antagonist DPCPX (2 mg·kg$^{-1}$, ip) can significantly inhibit the anti-convulsion effect of the HEA, whereas specific $A_{2A}$ receptor antagonist ZM241385 (1 mg·kg$^{-1}$, 5 mg·kg$^{-1}$, ip) had no significant effect on the anti-convulsion effect of the HEA. Thereby, we speculated that the HEA possibly participate in regulating convulsion effect by agonizing the $A_1$ receptor, the HEA can be used in clinical treatment and prevention of convulsion (FIGS. 2A-C).

Example 3. Application of the HEA in Cerebral Ischemia 3.1 Preparation of Tested Sample The dried *Cordyceps cicadae* was precisely weighed as raw material, and extracted by using 50% ethanol as solvent, 2 h/time, filtered, the filtrate were combined, to prepare a solution containing sample with a effective dose of 1500 mg/kg for subsequent use.

3.2 Animal Model and Administration Method

Using rat middle cerebral artery distal obstruction cerebral ischemia model. (1) according to rat weight, 10% chloral hydrate (3 ml/kg) was peritoneally injected to anaesthetize. (2) the rat lie on right side and fixed, 1 cm skin incision was cut at connection of inner canthus with external canal, fascia was isolated, muscle tissue, the skull was exposed; (3) a small amount of normal saline was sucked with cotton ball to wipe the skull to ac clear view; (4) fascia was isolated under operating microscope, and the skull was exposed, a hole with diameter of 2 mm circular was drilled at a sute 1/3 of spine; (5) the excess bone debris was washed by a small amount of normal saline, the meninge was push aside, and the middle cerebral artery MCA was exposed; (6) the rat lie in supine position and fixed, an incision was made along middle of throat, and arteria carotis communis CCA on both sides were isolate, pass through with a surgical suture, not ligated temporarily; (7) the MCA was found under operating microscope, burned by a monopolar coagulator, then wash and colled with normal saline; (8) immediately after coagulation, the arteria carotis communis on both sides was ligated, and blocked for 60 min; (9) the wound on head was stitched, after 1 hour the arteria carotis communis on both sides was ligated, and the skin was stitched, thus the modeling was complete.

SD rats were randomly divided into 7 groups: sham-operation group (1% DMSO, ip), model group, *Cordyceps cicadae* extract group 1500 mg/kg, HEA 5 mg/kg group, HEA 7.5 mg/kg group, HEA 12 mg/kg group, HEA 7.5 mg/kg+DPCPX 1 mg/kg group. In each group, the drug were peritoneally injected for one time respectively before 30 minutes of the dMCAO operation, in the sham-operation group and the model group 1% dimethyl sulfoxide were given, in the sham-operation group rat only craniotomy was conducted to expose the middle cerebral artery, the coagulation of middle cerebral artery peritoneal injection were nit conducted, and $A_1$ selective adenosine receptor antagonist DPCPX was peritoneally injected 10 minutes before drug administration.

3.3 Determination of Index 3.3.1 the neurologic function score of the animal in conscious were scored for the rat behaviour according to the Neurological Defects 4 Score in 5 Grade Method by Longa E Z et al [4] : 0 point: no significant neurologic function impairment; 1 point: unable to stretch forelimbs on opposite sides; 2 point: rolling to the opposite side when walking; 3 point: duping to the opposite side when walking; 4 point: unable to spontaneously walk, and loss of consciousness.

3.3.2 Determination of cerebral infarction area by TTC staining: after 24 hours of modeling, the rat was anaesthetize then the chest was opened to expose heart, and 250 mL of normal saline was perfused, then pulpotomy was conducted to remove the brain tissue, placed at −80 □ and frozen. The frozen rat brain was put into a brain cutting mold, 5 slices was cut from antiunion to polusoccipitalis (not including cerebellum), slice thickness was 2 mm. the brain slice was carefully put into a black box containing 2% TTC by tweezers, incubated 15 min at normal temperature, a digital camera was fixed 30 cm directly above the brain slice to take photo. The succinic dehydrogenase with the mitochondria in normal brain tissue reacted with the TTC reaction to present bright red, and the infarction region was not colored because of lack of mitochondria. The infarct size was represented by percentage of the infarction region in whole brain.

3.3.3 Brain histomorphological staining HE: after 24 hours of modeling, the rat was anaesthetized, the heart was perfused and brain tissue was removed and fixed in a 4% paraformaldehyde; desiccated, embedded, coronal sectioned, after slicing stained with hematoxylin-eosin.

3.3.4 TUNEL Detection of Brain Cortex Apoptosis

The brain tissue was removed and fixed in paraformaldehyde, after completion of parafin section, colored by TUNEL Method according to requirement of kit and washed by water, desiccated, vifrification, sealing.

3.4 Experiment Result

Experiment results show that HEA (7.5 mg/kg) significantly improve neurological symptom of dMCAO rat, meanwhile significantly reduce cerebral infarction area, and reduce the cerebral cortex tissue structure loosening caused by ischemia, and the cell number was significantly reduced etc, and the apoptosis rate in rat cerebral cortex infarction ischemic penumbra was significantly reduced. The above-described protective effects may be antagonized by selective adenosine $A_1$ receptor antagonist, suggesting that HEA has certain brain protective effect, and such a neuroprotective effect is likely induced by activating adenosine $A_1$ receptor (FIGS. 3A-D).

Example 4. Application of HEA in Parkinson's Disease 4.1 Preparation of Tested Sample The dried *Cordyceps cicadae* was precisely weighed as the raw material, extracted by using 50% ethanol as solvent, 2 hour/time, filtered, the filtrate were combined, to prepare a solution containing the sample with a effective dose of 1500 mg/kg for subsequent use.

4.2 Animal Model and Administration Method

24±1 g male C57BL/6 mice were randomly divided into six groups: control group, model group, *Cordyceps cicadae* extract group (1500 mg/kg) (the extract method can refer to Example 3), HEA (5 mg/kg, 10 mg/kg, 15 mg/kg) group. Using mouse PD model induced by 1-methyl-4-phenyl-1,2,6-tetrahydropyridine (MPTP), in *Cordyceps cicadae* crude extract group and HEA with different concentration group were respectively peritoneal injected for consecutive 14 days, and at Day 11, before 1 hour of drug administration, MPTP 30 mg/kg was peritoneally injected, for consecutive 4 days, after one day after the last administration, a behavior test of pole-climbing ability was conducted, after 4 days the rat wad killed by puling neck and the striatum was removed. The control group was given same amount of normal saline, the model group at Day 11, one hour before the normal saline was given, MPTP 30 mg/kg was peritoneally injected, for four consecutive days.

4.3 Determination of Index 4.3.1 Determining the Mouse Sports Ability by Pole-Climbing Method Heading down, the mouse was placed onto top of a wooden pole with a length of 50 cm, diameter of 10 mm, the time for the mouse clime from top to bottom along the pole was record, the time difference between before and after the modeling was calculate, and analyzed statistically.

4.3.2 Determining the number of the TH positive cellsd in Substantia nigra by immunohistochemical method.

After completion of behaviour detection, the heart was perfuse with 4% paraformaldehyde and the brain was removed, fixed, desiccated, embedded, and different parts in substantia nigra region were removed for coronal sectioned, tyrosine hydroxylase was used as specific marker for the neuron. The primary antibody is monoclonal mouse TH antibody (1;1000, Sigma), and the secondary antibody is Alexa fluor 488 fluorescence labeling goat anti-mouse (1;1000, Molecular Probes). Taking photo by a fluorescence microscope, and the TH positive cell in the substantia nigra were counted.

4.4 Test Result

Figure 4A:
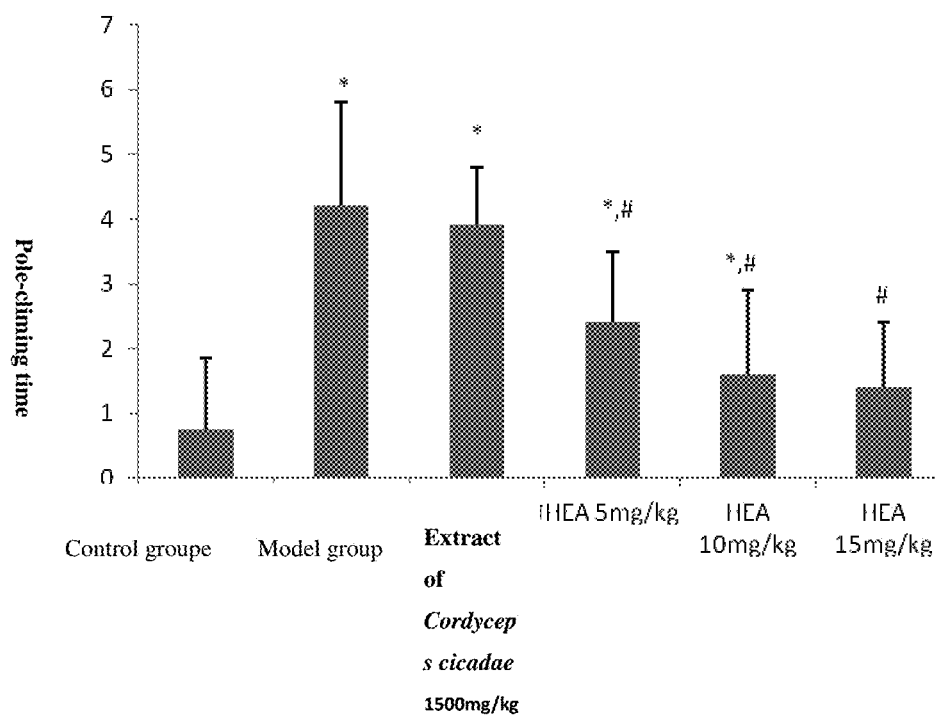
FIG. 4A shows effect of extract of *Cordyceps cicadae* (1500 mg/kg, ip), the HEA (5 mg/kg, 10 mg/kg, 15 mg/kg, ip) on mouse motor dysfunction induced by the MPTP (n=8; *P<0.05, **P<0.01 compared with control group; #P<0.05, ##P<0.01 compared with model group).
Figure 4B:
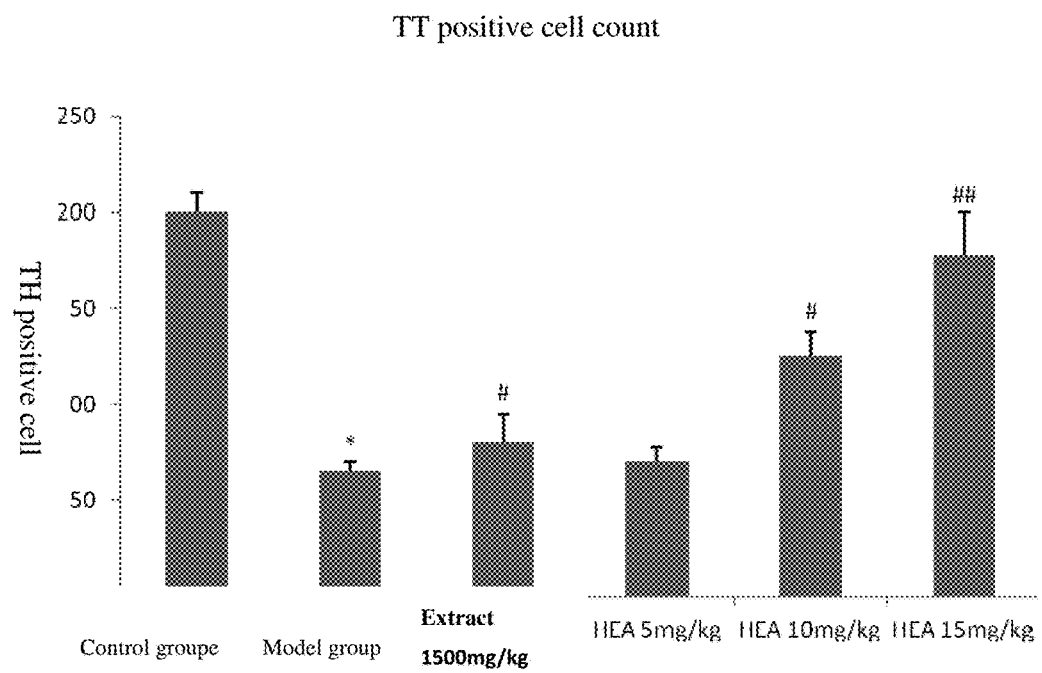
FIG. 4B shows effect of extract of *Cordyceps cicadae* (1500 mg/kg, ip), the HEA (5 mg/kg, 10 mg/kg, 15 mg/kg, ip) on dopaminergic neuron reduction caused by MPTP (n=8; *P<0.05, **P<0.01 compared with control group; #P<0.05, ##P<0.01 compared with model group).

Test result shows that *Cordyceps cicadae* extract and HEA (10 mg/kg, ip) can improve multilimb coordination ability of mouse to different degree, and increase number of the TH positive cells, suggesting HEA may be used in clinical treatment and prevention of the Parkinson's disease, and *Cordyceps cicadae* extract may have same function because it contains the HEA (FIGS. 4A-B).

Example 5. Application of HEA in Preparation of Sedative 5.1 Animal Grouping and Administration Method Male ICR mice were randomly divided into four groups, and adenosine $A_1R$ antagonist DPCPX was selected. The mice were divided into solvent group, HEA (15 mg/kg) group, DPCPX (4 mg/kg) and DPCPX+HEA (4 mg/kg+15 mg/kg) group; wherein in DPCPX+HEA group, the mice was peritonealelly injected with the antagonist, after 10 min the HEA was peritoneally injected.

5.2 Detecting Method

After 15 min of drug administration, the mice were put into a single opaque square spontaneous activity box (50 cm×50 cm×40 cm), and foot grating number within 5 min was recorded by video camera. Calculating on the basis of four limbs of the mouse entering the same lattice, as the activity index of the animal.

5.3 Experiment Result

Figure 5:
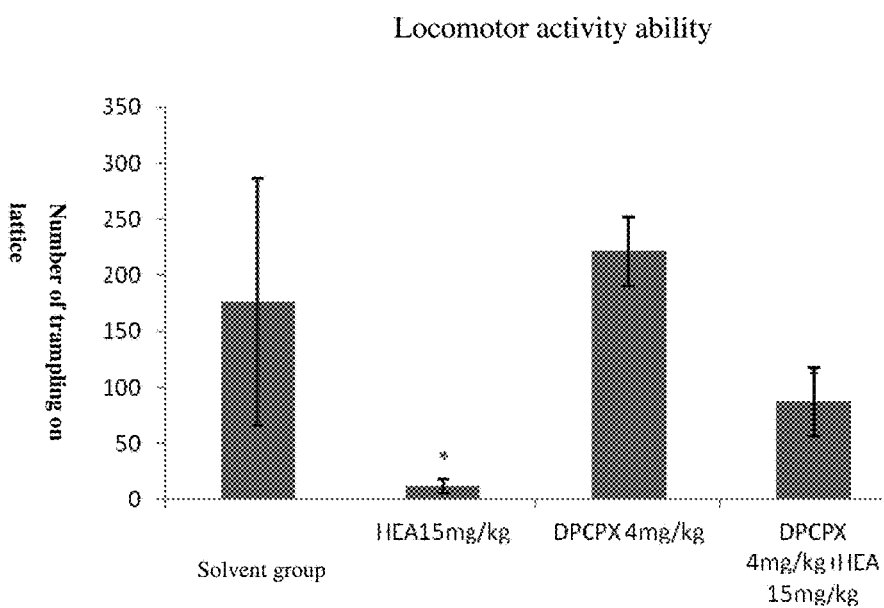
FIG. 5 shows effect of the HEA in combination with adenosine receptor on mouse spontaneous activity, the result shows that HEA (15 mg/kg) can significantly reduce spontaneous activity number of normal mouse within 5 min, under the effect of DPCPX (4 mg/kg), sedation of the HEA is significantly antagonized (n=8; *P<0.05, **P<0.01 compared with solvent group; #P<0.05, ##P<0.01 compared with drug group).

The inhibiting effect of HEA (15 mg/kg, ip) to mouse spontaneous activity was significant. This suggests that HEA may produce sedative effect in nervous system (FIG. 5).

Example 6. Application of HEA in Preparation of Hypnotics 6.1 Animal Grouping and Administration Method Male ICR mice were randomly divided into four groups, respectively control group, positivediazepam (1 mg/kg) group, HEA (25 mg/kg) group and DPCPX+HEA (2 mg/kg+25 mg/kg) group. After intragastric administration to the mice 30 min, the animals of each group were peritoneally injected with threshold dose of pentobarbital sodium 50 mg/kg.

6.2 Detection of Index:

Regarding the mouse righting reflex disappear for 1 min within 15 min as the hypnagogic criterion, sleep latency and sleep duration were recorded for the mice in each group.

6.3 Experiment Result

Figure 6:
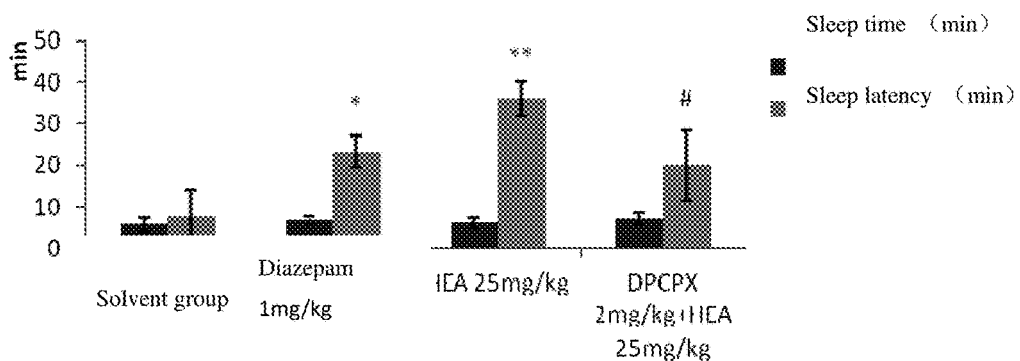
FIG. 6 shows that the HEA (25 mg/kg, sc) when used alone extends mouse sleep time induced by threshold dose of pentobarbital sodium to a certain degree, and has no significant effect on sleep latency, when used in combination with adenosine receptor antagonist, the hypnosis effect of the HEA is significantly inhibited (n=8; *P<0.05, **P<0.01 compared with solvent group; #P<0.05, ##P<0.01 compared with drug group).

HEA (25 mg/kg, sc) extended sleep time of the mice induced by threshold dose of pentobarbital sodium to a certain degree, but there was no statistical difference in sleep latency compared with control group, suggesting the Cicada fungus extract HEA has certain synergistic action with pentobarbital sodium (FIG. 6).

Example 7: Application of HEA in Analgesia 7.1 Animal Grouping and Administration Method Clean male Kunming mice, weight 18-22 g, selecting adenosine AiR antagonist DPCPX. The mice were divided into solvent group, HEA (15 mg/kg) group, DPCPX (1 mg/kg) and DPCPX+HEA (1 mg/kg+15 mg/kg) group; wherein in DPCPX+HEA group, the mouse was peritoneally injected with antagonist, after 10 minutes, the HEA was peritonealy injected.

7.2 Detecting Method

Using writhing method, the treatment dose was given, after 30-40 minutes, 0.7% acetic acid was peritoneally injected, and writhing number of the white mouse within 15 minutes was recorded, calculating the reduction number of pain writhing response induced by 0.7% acetic acid by the HEA.

7.3 Experiment Result

Figure 7:
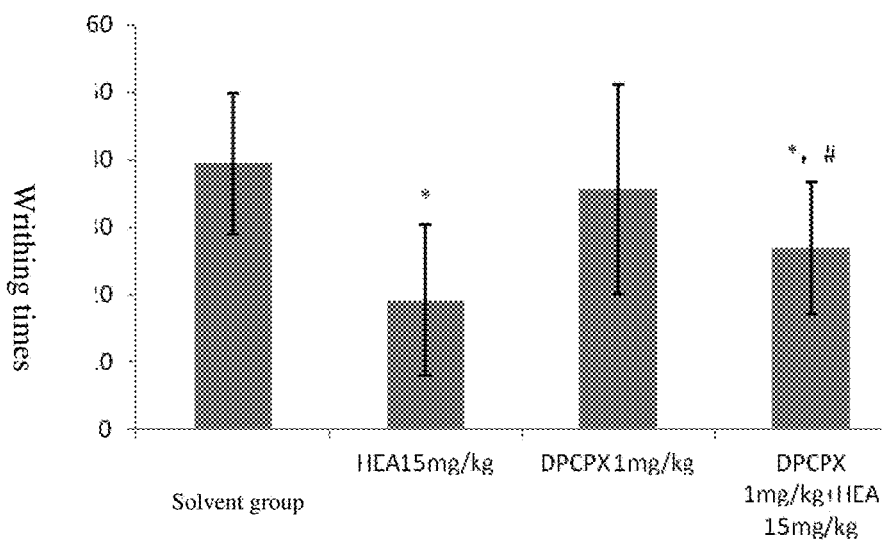
FIG. 7 shows effect of HEA in combination with adenosine receptor on reduction of pain mouse writhing number, the result shows that the HEA (15 mg/kg) can significantly reduce writhing number of the mice, under the action of DPCPX (1 mg/kg), the analgesic effect of the HEA is significantly antagonized (n=8; *P<0.05, **P<0.01 compared with solvent group; #P<0.05, ##P<0.01 compared with drug group HEA 15 mg/kg).

HEA (15 mg/kg, ip) significantly reduced the writhing number of pain mouse, demonstrating that the analgesia effect of the HEA is significant, and the analgesic effect was reduced by adding adenosine $A_1$ receptor antagonist, suggesting that the analgesia effect of the HEA is possibly via agonizing adenosine $A_1$ receptor (FIG. 7).

Example 8. Application of the HEA or the Medicinal Fungus and Extract Containing the HEA on the Preparation of Drugs for Treatment and Prevention of Addiction 8.1 Preparation of Tested Sample The dried *Cordyceps cicadae* was precisely weighed as the raw material, and marked as the sample A, extracted by using 50% ethanol as the solvent for 2 h/time, filtered, the filtrate were combined, isolated by successively passing through membrane, purified with acroporous resin and Sephadex LH20 column, extracted in a stepwise manner, respectively obtaining samples of B, C, D. They were respectively prepared to solutions in which effective dose of each ingredient (HEA) being 1500 mg/kg, 750 mg/kg, 100 mg/kg, 20 mg/kg for subsequent use.

8.2 Animal Grouping and Administration Method

Clean male Kunming mice, weight 18~22 g, were divided into control group, morphine group, sample group (A: 1500 mg/kg, B: 750 mg/kg, C: 100 mg/kg, D: 20 mg/kg). Natural preference test (d−2, d−1, d0): Three days before the experiment, let the mice freely move in a box for 15 min, according to rat natural preference to black box, a white box was selected as accompanying box, residence time in the white box of each rat (d−1, d0) were recorded, using average value of the test results of two days as base value of the rat in the accompanying box. Cpp establishment: the morphine treated group: at d1, d3, d5, d7, after hydrochloric acid (10 mg/kg, ip) was peritoneally injected, trained in the white box for 50 minutes, at d2, d4, d6, d8 same volume of normal saline was peritoneally injected, then trained in the black box for 50 min. In drug group, morphine was injected every day, and the normal saline group ware given normal saline for 8 days. Cpp expression: at Day 9, heading down, the rat was placed at the boundary of the two boxes without any treatment, let is freely move in the two boxes for 15 minutes, and the residence time in the white box of the rat was record; Cpp extinction: from Day 10, the experiment group and control group were given normal saline, at d10, d12, d14, d16 trained in the white box for 50 min, at d11, d13, d15, d17 trained for 50 min; at d18 m heading down, the rat was placed at the boundary of the two boxes without any treatment, let it freely move in the two boxes for 15 minutes, the residence time in the white box of rat was recorded; Cpp readdiction: at d19, in morphine group was given 5 mg/kg, in drug group, 15 min before morphine administration, the mice in each group were tenderly placed at the boundary of the two boxed heading to the white box and freely move for 15 minutes, and the activities were recorded.

8.3 Detection Index

Position preference index: the residence time in the white box of the mice at different time were recorded, and the effect of the HEA or medicinal fungus and extract containing the HEA on mouse CPP induced by morphine at different addiction stages were analyzed.

8.4 Test Result

Figure 8A:
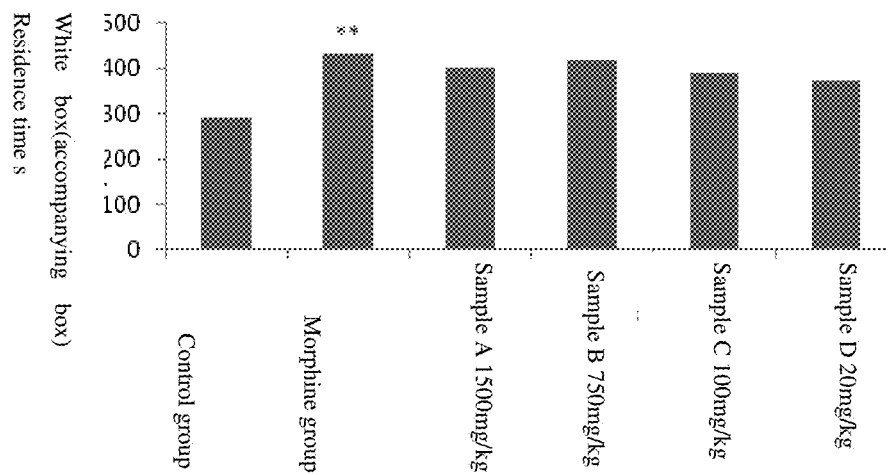
FIG. 8A shows effect of the HEA and *Cordyceps cicadae* containing the HEA and its extract on morphine induced addiction in CPP establishing stage (n=8; *P<0.05, **P<0.01 compared with control group).
Figure 8B:
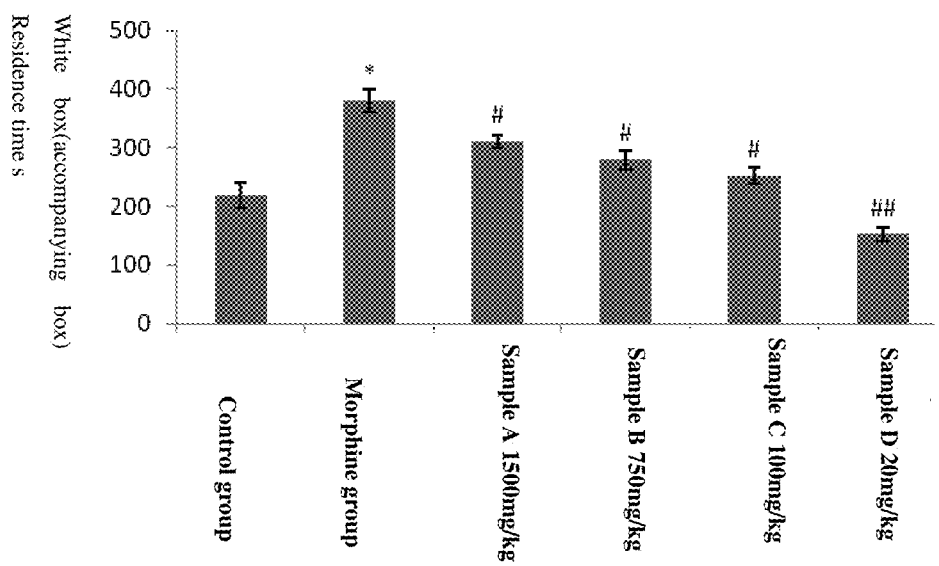
FIG. 8B shows effect of HEA and *Cordyceps cicadae* containing the HEA and its extract on morphine induced readdiction in a CPP burning and readdiction stage (n=8; *P<0.05, **P<0.01 compared with control group; #P<0.05, ##P<0.01 compared with morphine group).
Figure 9A:
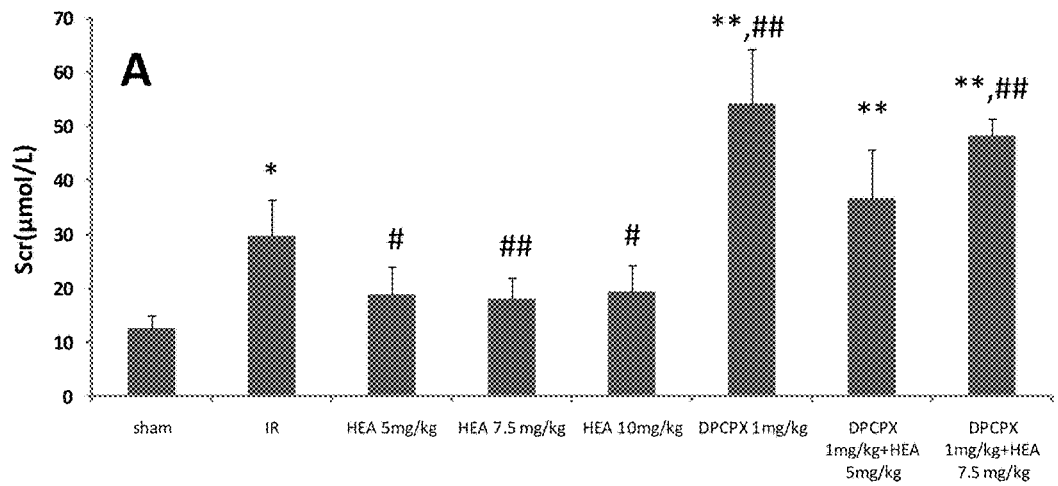
FIGS. 9A-B shows effect of the HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on serum Scr (A) and BUN (B) level after 24 h of mouse ischemia reperfusion (n=5; *P<0.05, **P<0.01 compared with sham-operation group; #P<0.05, ##P<0.01 compared with IR group). Compared with the sham-operation group: Scr and BUN levels are significantly increased in IR group. Compared with in IR group: HEA pretreated mice (5 mg/kg, 7.5 mg/kg, 10 mg/kg) significantly reduce Scr and BUN levels; pretreatment with selective ALAR antagonist DPCPX (1 mg/kg) and DPCPX (1 mg/kg)+HEA (7.5 mg/kg) respectively significantly increase Scr and BUN levels, whereas there is no significant difference (P>0.05) in Scr and BUN levels between the three groups of DPCPX (1 mg/kg), DPCPX (1 mg/kg)+HEA (5 mg/kg) and DPCPX (1 mg/kg)+HEA (7.5 mg/kg).
Figure 9B:
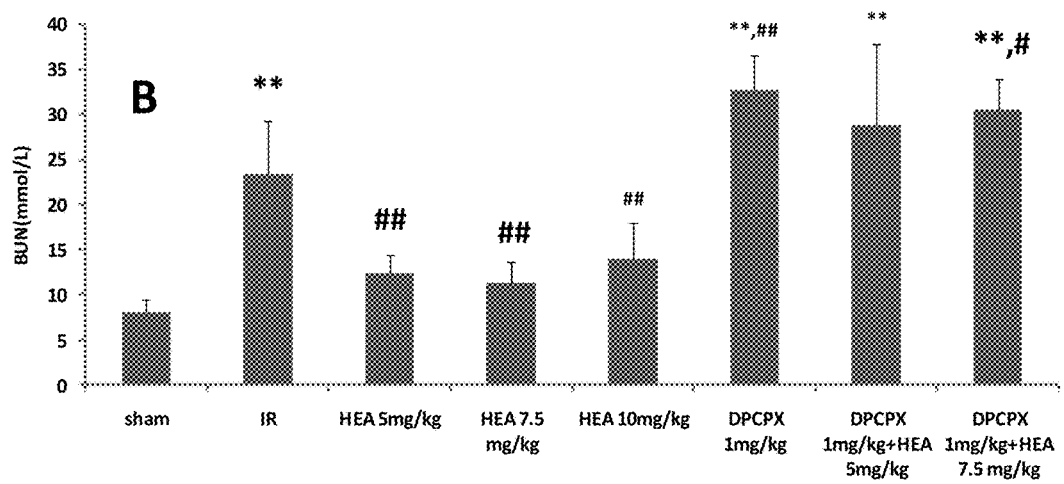
Figure 9C:
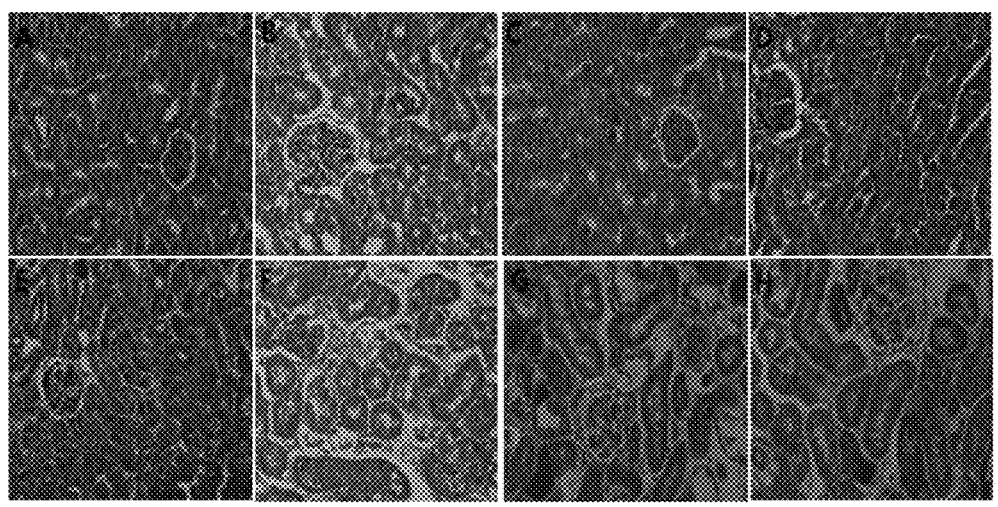
FIG. 9C shows effect of the HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on kidney histopathological changes after mouse ischemia reperfusion (HE×400). Note: A: sham-operation group; B: IR group; C: HEA 2.5 mg/kg group; D: HEA 5 mg/kg group; E: HEA 7.5 mg/kg group; F: DPCPX (1 mg/kg) group; G: DPCPX (1 mg/kg)+HEA (5 mg/kg); H: DPCPX (1 mg/kg)+HEA (7.5 mg/kg). The kidney tissue structure in the sham-operation group (A) is essentially normal, only local renal tubular epithelial cell degeneration, exfoliated necrosis cell and vacuolar degeneration in local kidney tubules can be seen. Compared with kidney of mice in the sham-operation group, tissue many renal tubular epithelial cell swelling and vacuolar degeneration are seen in kidney of the IR group (B), and cell piecemeal necrosis, exfoliation, kidney tubules dilatation are seen at severe part, in some place epithelial cell debris and brush border exfoliation are seen. In HEA 2.5 mg/kg group (C), HEA 5 mg/kg group (D) and HEA 7.5 mg/kg group (E) pathological changed of the specimen are significantly reduced compared with IR group, and swelling, exfoliation and vacuolar degeneration occur in only a part of the cells, necrosis cells is less, the shape of kidney tubules is good. On the contrary, pretreatment with selective $A_1AR$ antagonist DPCPX before IR impairment can aggravate tissue necrosis, the celles are essentially exfoliated, kidney tubules are dilatated, there is little structurally complete renal tubular epithelial cells. DPCPX+HEA also aggravates kidney tissue necrosis.
Figure 9D:
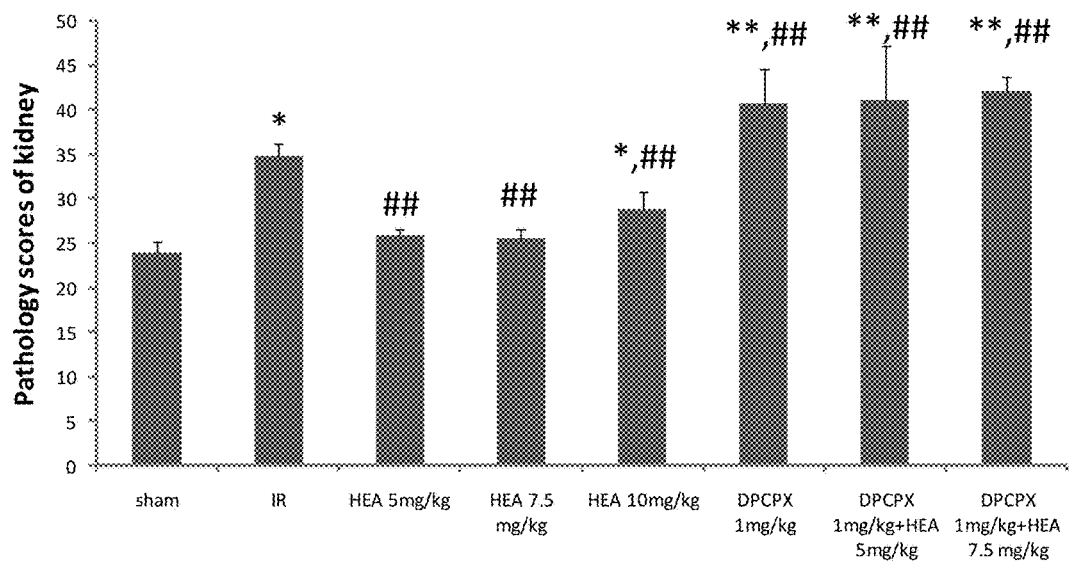
FIG. 9D shows kidney pathological score (n=5; *P<0.05, **P<0.01 compared with sham-operation group; #P<0.05, ##P<0.01 compared with IR group); the renal tubulointerstitial impairment score in the IR group is significantly increased compared with the sham-operation group (P<0.01). Compared with IR group, the renal tubulointerstitial impairment scores are significantly reduced in HEA 5 mg/kg group, HEA 7.5 mg/kg group and HEA 10 mg/kg group (P<0.01, P<0.01, P<0.01). On the contrary, compared with the IR group, pretreatment with DPCPX 1 mg/kg, DPCPX (1 mg/kg)+HEA (5 mg/kg) and DPCPX (1 mg/kg)+HEA (7.5 mg/kg) significantly increase renal tubulointerstitial impairment scores (P<0.01, P<0.01, P<0.01), and there are no significant difference in the renal tubulointerstitial impairment score between these three groups (P>0.05).
Figure 9E:
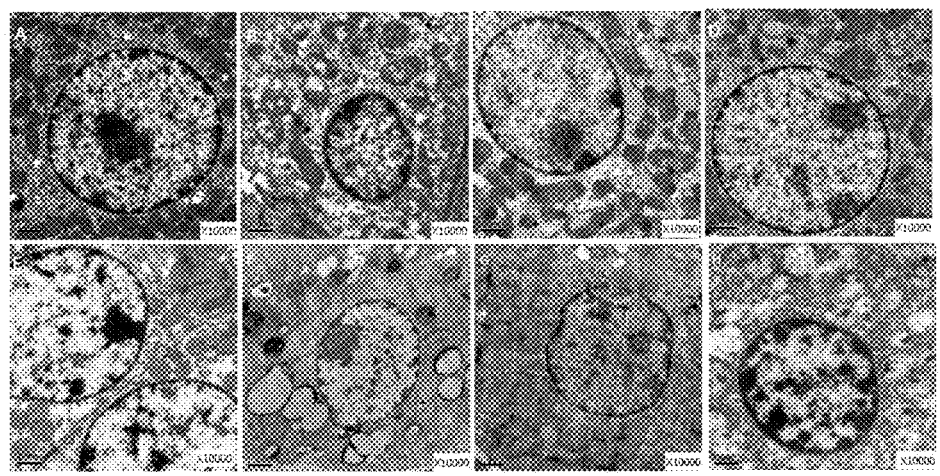
FIG. 9E qualitatively observes by electron microscope the effect HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on mice renal tubular epithelial cell apoptosis. Note: A: the sham-operation group; B: the IR group; C: HEA 2.5 mg/kg group; D: HEA 5 mg/kg group; E: HEA 7.5 mg/kg group; F: DPCPX (1 mg/kg) group; G: DPCPX (1 mg/kg)+HEA (5 mg/kg); H: DPCPX (1 mg/kg)+HEA (7.5 mg/kg). In the sham-operation group (A) the nucleus is complete. The structure oif nucleus and organelle are clearly visible, two layers in the nuclear membrane, mitochondria is complete, mitochondrial cristae is clear. In the IR group (B), karyopyknosis, swelling, and degeneration are observed; there is no any one structurally complete mitochondria; partial karyolysis; chromatin concentrates to block and margination; mitochondria Vacuole; cell border is not smooth; cell membrane is vague and wrinkled; chromatin is sparse and fine granular, distributed irregularly, border is vague, cytoplasm is swelling, organelle structure is destroyed. In HEA 5 mg/kg group (C), the entirety is improved compared with ischemia reperfusion group, the structure of a part of mitochondria is complete, the mitochondrial cristae is clear. But, there are large lipid vesicles. In HEA 7.5 mg/kg group (D), the bilayer in the nuclear membrane is more clear compared with IR group and HEA 5 mg/kg group (C), and most of the mitochondria are normal, mitochondrial cristae is more clear, but there are some lysosomes. In HEA 10 mg/kg group (E), mitochondria protection is more clear than the IR group, most of the mitochondria structure are complete, but swelling occurs in some mitochondria. If pretreated with selective $A_1AR$ antagonist DPCPX (F) before ischemia, there are essentially no mitochondria with complete structure, a great number of lysosome and lipid vesicle appear. If pretreated with drug combination DPCPX+HEA (G, H) before ischemia, nucleus karyopyknosis, swelling, and chromatin bordering occur, and there is essentially no mitochondria with complete structure, the apoptosis degree is more severe than the IR group.
Figure 9F:
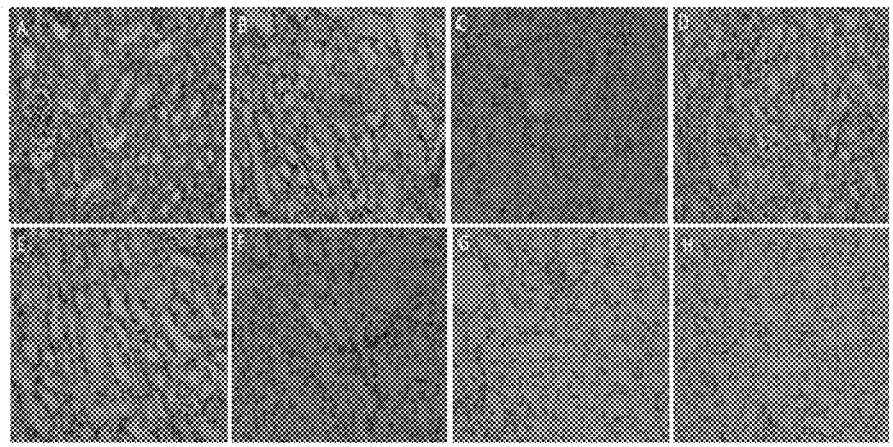
FIG. 9F quantitatively observed by TUNEL the effect of HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on mouse renal tubular epithelial cell apoptosis (TUNEL×400). Note: A: sham-operation group; B: IR group; C: HEA 2.5 mg/kg group; D: HEA 5 mg/kg group; E: HEA 7.5 mg/kg group; F: DPCPX (1 mg/kg) group; G: DPCPX (1 mg/kg)+HEA (5 mg/kg); H: in DPCPX (1 mg/kg)+HEA (7.5 mg/kg) sham-operation group, apoptosis occur in very few cells of the kidney tissue, whereas in IR group apoptosis are significantly increased, and compared with the IR group, apoptosis number is reduced in HEA treated group, but more than sham-operation group. The apoptotic cells in pretreatment with selective $A_1AR$ antagonist DPCPX group and drug combination DPCPX+ HEA group are significantly increased, compared with the IR group.
Figure 9G:
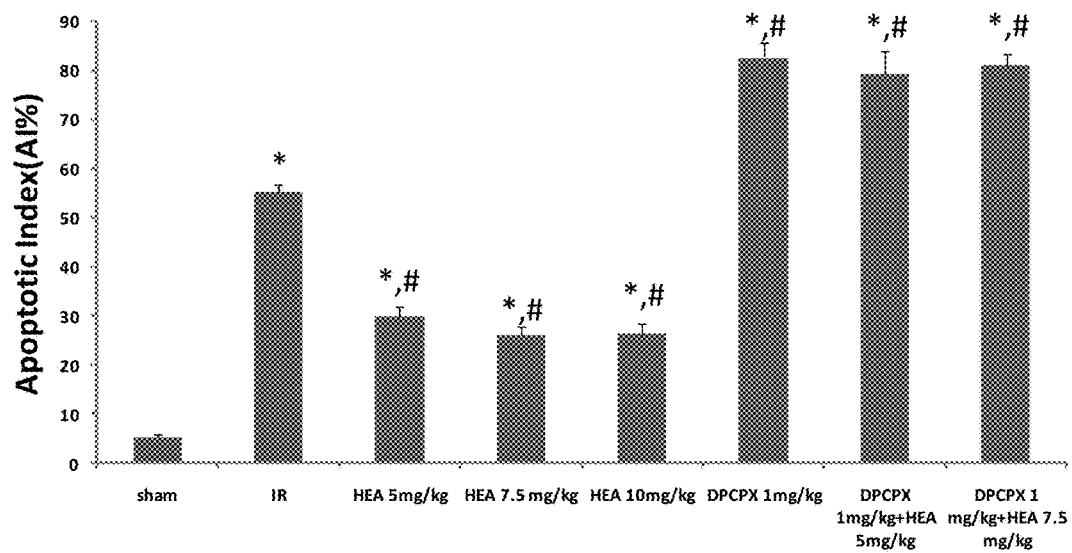
FIG. 9G TUNEL apoptosis index (n=5; *P<0.05, **P<0.01 compared with sham-operation group; #P<0.05, ##P<0.01 compared with IR group) in IR group is significantly increased compared with the sham-operation group (P<0.05); the apoptosis index in HEA-treated group (5 mg/kg, 7.5 mg/kg, 10 mg/kg) is significantly less than IR group (P<0.01). The apoptosis index of pretreatment with selective $A_1AR$ antagonist DPCPX (1 mg/kg) and drug combination [DPCPX (1 mg/kg)+HEA (5 mg/kg); DPCPX (1 mg/kg)+HEA (7.5 mg/kg)] are significantly greater than IR group (P<0.01).
Figure 9H:
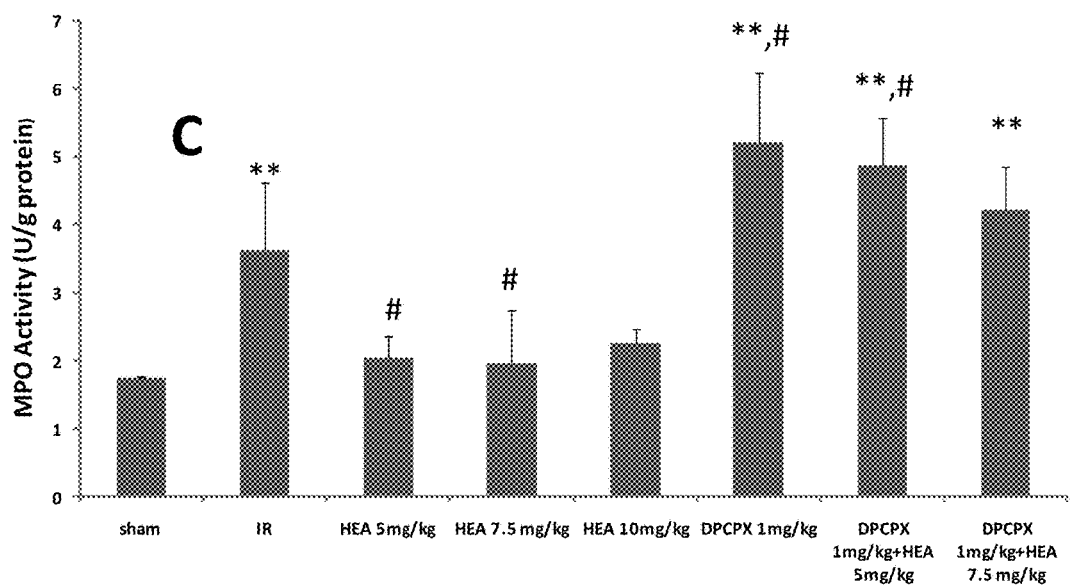
FIG. 9H shows the effect of HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on mouse myeloperoxidase (MPO) activity (n=5; *P<0.05, **P<0.01 compared with the sham-operation group; #P<0.05, ##P<0.01 compared with the IR group). Compared with the sham-operation group: MPO activity in IR group mouse renal cortex is significantly increased (P<0.01). Compared with IR group: the MPO activity of C57 mouse being pretreated with HEA 5 mg/kg and 7.5 mg/kg before IR impairment is significantly reduced (P<0.05); on the contrary, pretreatment with selective $A_1$ AR antagonist DPCPX (1 mg/kg) and DPCPX (1 mg/kg)+HEA (5 mg/kg) significantly increase MPO activity (P<0.05). there is no statistically significant difference in MPO activity between three groups of DPCPX (1 mg/kg) group, DPCPX (1 mg/kg)+HEA (5 mg/kg) group and DPCPX (1 mg/kg)+HEA (7.5 mg/kg) group (P>0.05).
Figure 9I:
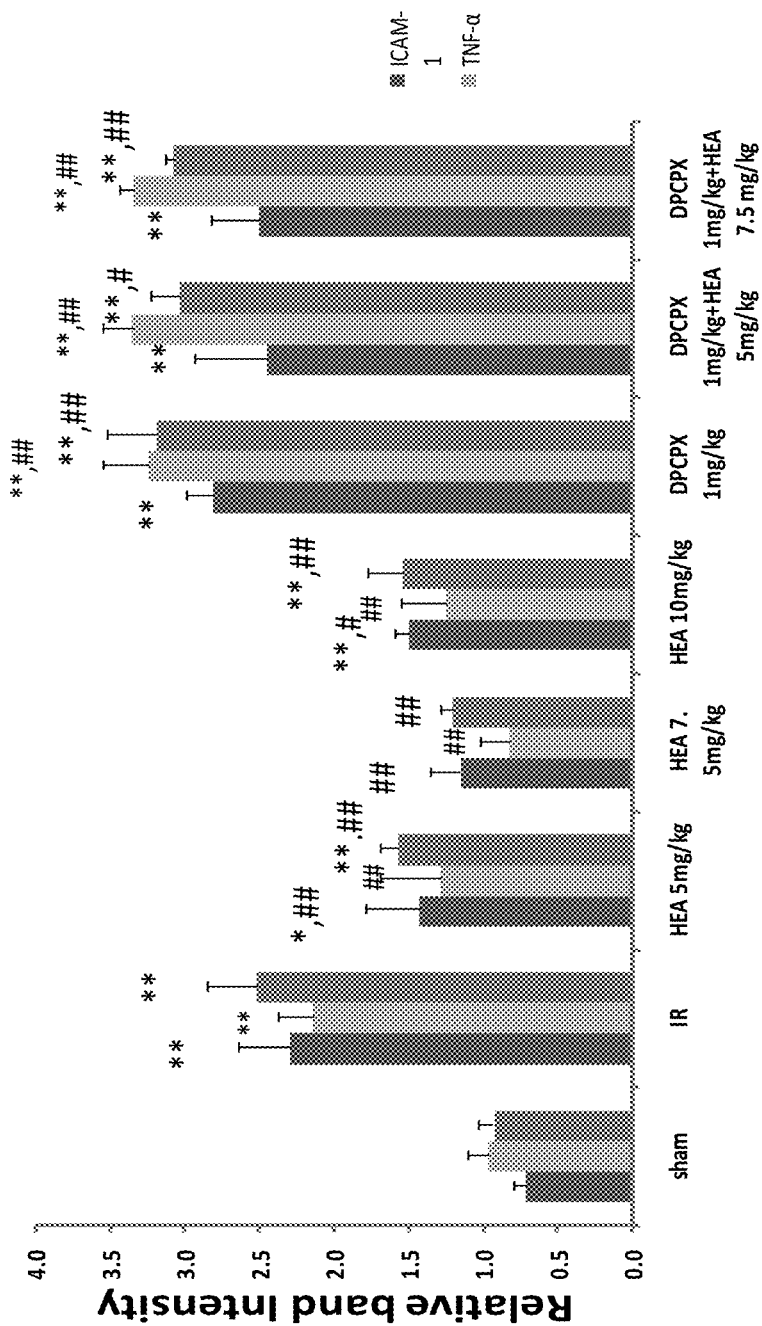
FIG. 9I shows the effect of HEA (5 mg/kg, 7.5 mg/kg, 10 mg/kg, ip), selective $A_1AR$ antagonist DPCPX 1 mg/kg, drug combination group DPCPX (1 mg/kg)+HEA (5 mg/kg) and DPCPX (1 mg/kg)+HEA (7.5 mg/kg) on ICAM-1, IL-1β, TNF-α mRNA gene expression in mouse renal cortex (n=5; *P<0.05, **P<0.01 compared with sham-operation group; #P<0.05, ##P<0.01 compared with the IR group). Compared with the sham-operation group, mRNA expression of ICAM-1, TNF-α and IL-1β in renal cortex in the IR group mouse were significantly increases (P<0.01). Compared with IR group: pretreatment with HEA 5 mg/kg, 7.5 mg/kg and 10 mg/kg significantly reduce the high expression of mRNA of ICAM-11, TNF-α and IL-1β. On the contrary, pretreatment with selective $A_1AR$ antagonist DPCPX (1 mg/kg), DPCPX (1 mg/kg)+HEA (5 mg/kg) and DPCPX (1 mg/kg)+HEA (5 mg/kg) respectively increase expression amount of mRNA of proinflammatory cytokine ICAM-1, TNF-α and IL-1β, wherein mRNA expression amount of TNF-α and IL-1β are significantly increase, whereas increase of ICAM-1 is not statistically significant. In addition, the gene expressions of proinflammatory cytokine between three groups of DPCPX group and drug combination DPCPX+HEA group are not statistically significant (P>0.05).

Experiment result shows that in forming period by multiple administration of *Cordyceps cicadae* sample A or its stepwise extract (B,C,D) had no significant difference on the residence time in the accompanying box of the mouse induced by morphine, but in withdrawal period after treatment with *Cordyceps cicadae* sample A or stepwise extract sample (B,C) the residence time in the accompanying box time was significantly lower than morphine group, especially, the residence time in the accompanying box of sample D is very significantly lower than morphine group, suggesting that HEA can be used in drug-seeking behaviour after withdrawal, and it had certain anti-addiction (FIGS. 8A-B).

Example 9: Application of HEA in Anti-Renal Failure 9.1 Animal Grouping, Modeling and Administration Method Male C57BL/6 mice 20-25 g, after one week of adaptive feeding to the animals, were randomly divided into eight groups: sham-operation group, IR group, HEA 5 mg/kg group, HEA 7 mg/kg group, HEA 10 mg/kg group, DPCPX (1 mg/kg) group, DPCPX (1 mg/kg)+HEA (5 mg/kg) group and DPCPX (1 mg/kg)+HEA (7.5 mg/kg) group.

The mouse was weighed before operation, then peritoneally injected with pentobarbital sodium 50 mg/kg to anaesthetize the mouse, abdomen was opened by ventromedial incision, blunt dissection and the kidney pedicle was sufficiently exposed, renal ischemia was induced by clapping two side kidney pedicle with non-invasive bulldog clamp, the color of kidney change from bright red to purple black immediately, determination method of success of the experiment model can refer to the methods in literature 7 and 8. At time of 30 min of ischemia the bulldog clamp was loosened, the perfuse was restored, the color of kidney changed gradually from dark red to bright red, showing re perfusion was successful. The wound was stitched. The animals were freely fed water and food.

In the sham-operation group, the mice only received operation of abdomen open, kidney pedicle and abdomen suture. The kidney IR mode were made for the mice in the remaining groups. In each drug group, before 15 minute of ischemia, the drug with corresponding concentration was speritoneally injected, in drug combination group, 15 minutes before ischemia, the drugs were given simultaneously.

9.2 Detection Index 9.2.1 Kidney Function Test

At 24 hours after Reperfussion, the mouse was again anaesthetized, obtaining the venous blood. Using full-automatic biochemical analysis systems (Dimension Xpand plus, from Siemens AG), the Scr (serum creatinine) and BUN (blood urea nitrogen) levels were detected respectively by chrysolepic acid rate method and enzymatic rate.

9.2.2 Kidney Histopathologic Examination

At 24 hours after reperfusion, the mouse was anaesthetized again, the kidney specimen was obtained. The kidney specimen is fixed by 10% formaldehyde solution, paraffin embedded, sectioned, hematoxylin-eosin staining (HE), and the kidney histopathological change was observed under optical microscope.

9.2.3 Preparation of Electron Microscope Section and Subcellular Observation.

The section was observed using Transmission Electron Microscope (H7500, from Hitachi Co. limited). The observation was conducted in Electron Microscoper Room of Wenzhou Medical University.

9.2.4 Analyzing Apoptosis by TUNEL Method

Fetching a part of the stored kidney tissue, conventional paraffin embedded 4 μm of section. Operate according to the method of the specification in kit. Judgement of the positive staining result: the positive cell exhibited that nucleus was tan or brown. Randomly selecting 10 400-fold visual fields, calculate apoptosis index AI %=positive cell number/total number of all cell in the visual field×100%.

9.2.5 MPO Analysis

The MPO analysis was conducted according to the specification in the kit. 9.2.6 Real time quantitative PCR analysis of gene expression of ICAM-1, TNF-α and IL-1β; the sequence of primer used in RT-PCR reaction system is as follow:

```
GAPDH:
upstream
                                      (SEQ ID NO: 1)
5'-GAGACCTTCAACACCCCAGC-3';

downstream
                                      (SEQ ID NO: 2)
5'-ATGTCACGCACGATTTCCC-3';

ICAM-1:
upstream
                                      (SEQ ID NO: 3)
5'-TCTTCTGAGCGGCGTCG-3';

downstream
                                      (SEQ ID NO: 4)
5'-TTGCCAGGTCCAGTTCCC-3';

IL-1β:
upstream
                                      (SEQ ID NO: 5)
5'-TGGGAAACAACAGTGGTCAGG-3'.

Downstream
                                      (SEQ ID NO: 6)
5'-CATCAGAGGCAAGGAGGAAAAC-3';

TNF-α:
upstream
                                      (SEQ ID NO: 7)
5'-AACTTAGAAAGGGGATTATGGCT-3';

downstream
                                      (SEQ ID NO: 8)
5'-TCAGGGAAGAATCTGGAAAGGT-3'.
```

PCR amplification reaction system: IQ SYBR Green Super mix 12.5 μL, Forward primer (10 μmo/L) 1 μL, Reverse primer (10 μmol/L) 1 μL, cDNA (water was added to dilute to same level) 10.5 μL. Reaction conditions: 50.0° C. 3 min, 95.0° C. 3 min; 95.0° C. 10 s, 60.0° C. 10 s, 72.0° C. 20 s, totally 5 cycles. The statistics and calculation of experiment results was automatically conducted fluorescence quantitative PCR analyzing software BIO-RAD CFX Manager. Target gene mRNA expression level was calculated by 2-ΔΔCt method, and standardized using the GAPDH mRNA in corresponding specimen a standard.

9.3 Test Result

By detecting serum Scr and BUN level and observing kidney histopathological change, it is conformed that extract of Cordyceps cicadae N(6)-(2-hydroxyethyl)adenosine has protective effect to mouse kidney ischemia reperfusion impairment, and speculate the N(6)-(2-hydroxyethyl)adenosine effect mechanism by drug combination method of adding selective $A_1AR$ antagonist DPCPX, it is speculated that N(6)-(2-hydroxyethyl)adenosine may scavenge oxygen free radical, reduce lipid peroxidation reaction, reduce apoptosis, reduce release of inflammatory factors, protect ischemia-reperfused kidney by agonizing adenosine $A_1AR$ (FIGS. 9A-I).

The invention claimed is:

1. A method for treating a condition comprising administering N(6)-(2-hydroxyethyl)-adenosine (HEA) to a subject, wherein the condition is convulsion, pain, apoplexia, Parkinson's disease, or opioid drug addiction receptor; said HEA is administered in the amount of 10-15 mg/kg of subject body weight and treats the condition via the adenosine A1 receptor.

2. The method according to claim 1, wherein said HEA is derived from the group consisting of *Cordyceps, Cordyceps militaris, Paecilomyces cicadae* fungus and culture extract of the fungus.

3. The method according to claim 1, wherein said HEA is derived from the group consisting of *Cordyceps cicadae, Cordyceps militaris, Cordyceps sinensis* and extract of its artificial culture.

\* \* \* \* \*